US007081139B2

(12) United States Patent
Joerger et al.

(10) Patent No.: US 7,081,139 B2
(45) Date of Patent: Jul. 25, 2006

(54) ANTIMICROBIAL POLYESTER-CONTAINING ARTICLES AND PROCESS FOR THEIR PREPARATION

(75) Inventors: Melissa C. Joerger, Newark, DE (US); Ronald F. Koniz, Greenville, NC (US); Subramaniam Sabesan, Wilmington, DE (US); John Pennias, Hockessin, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 491 days.

(21) Appl. No.: 10/205,660

(22) Filed: Jul. 25, 2002

(65) Prior Publication Data

US 2003/0017194 A1 Jan. 23, 2003

Related U.S. Application Data

(63) Continuation-in-part of application No. 10/143,380, filed on May 10, 2002, now abandoned.

(60) Provisional application No. 60/290,297, filed on May 11, 2001.

(51) Int. Cl.
*A61F 13/15* (2006.01)
*A61K 9/70* (2006.01)
*D01D 5/08* (2006.01)

(52) U.S. Cl. ............... 8/115.54; 264/178; 424/443; 428/372; 525/54.2; 604/372

(58) Field of Classification Search ............... 264/182, 264/184, 178; 8/115.54; 424/443; 428/372; 525/54.2; 604/372
See application file for complete search history.

(56) References Cited

U.S. PATENT DOCUMENTS

| 3,594,216 | A | | 7/1971 | Cleary et al. |
| 3,671,379 | A | | 6/1972 | Evans et al. |
| 5,464,666 | A | | 11/1995 | Fine et al. |
| 6,524,508 | B1 | * | 2/2003 | Ohnishi et al. ............. 264/182 |
| 6,551,705 | B1 | * | 4/2003 | Ohnishi et al. ............. 428/372 |
| 6,586,529 | B1 | * | 7/2003 | Mumick et al. ............. 525/221 |
| 2003/0091612 | A1 | | 5/2003 | Sabesan |
| 2003/0152632 | A1 | | 8/2003 | Sabesan et al. |
| 2004/0247662 | A1 | | 12/2004 | Dow et al. |
| 2005/0012630 | A1 | | 1/2005 | Misato |

FOREIGN PATENT DOCUMENTS

| EP | 1 170 308 A | 1/2002 |
| JP | 0022772 | 2/1996 |
| JP | 9-291478 A | 11/1997 |
| WO | WO 00/49219 | 8/2000 |
| WO | WO 2005/019315 A1 | 3/2005 |

OTHER PUBLICATIONS

Man Woo Huh et al., Surface Characterization and Antibacterial Activity of Chitosan-Grafted Poly(ethylene terephthalate) Prepared by Plasma Glow Discharge, Journal of Applied Polymer Science, vol. 81:2769-2778, 2001.
Ga-er Yu et al., Degree of Acetylation of Chitin and Extent of Grafting PHB on Chitosan Determined by Solid State 15N NMR, Macromolecules, vol. 32:518-520, 1999.
Dictionary of Fiber & Textile Technology, Hoechst Celanese Corp., Charlotte, NC (1990), p. 8.
Ullman's Encyclopedia of Industrial Chemistry, 5th Edition, Wolfgang Gerhartz, vol. A10, Fed. Republic of Germany 1987, H. Lucker et al., pp. 511-566.
S. Matsukawa et al., Modification of Polyester Fabrics Using Chitosan, Sen-I Gakkaishi, vol. 51(1):51-56, 1995.
Qu et al., Surface modification of high density polyethylene tubes by coating chitosan, chitosan hydrogel and heparin, Polymer Bulletin, vol. 46:223-229, 2001.
H. Shin et al., Effect of Ultraviolet Irradiation on Fixation of Chitosan on Cotton and Poly(Ethylene Telephthalate) Fabrics, Sen-I Gakkaishi, vol. 54(8):400-406, 1998.
Hisashi Tanaka et al., Uber die Synthese und Chelatkomplexe von 2-Pyrrolylmethyleniminen. II. Chemical and Pharmaceutical Bulletin, vol. 10(6):435-439, 1962.
B. Emmert et al., Uber innere Komplexsalze einiger Pyrrol-Derivate, Chemische Berichte, vol. 62:1733-1738, 1929.
K-N Yeh et al., Synthesis and Properties of Some Metal Chelates of 2-Pyrrolealdimines, Inorganic Chemistry, American Chemical Society, vol. 6(4):830-833, 1967.
Hisashi Tanaka et al., Uber die Synthese und die Chelatkomplexe von N-2-Pyrrolylmethylenaminen. I. Chemical & Pharmaceutical Bulletin, vol. 9:588-592, 1961.
Chemical Abstracts Online, Krowczynski, Adam et al., Metal complexes of pyrrole derivatives and method of their preparation, Database Accession No. 129:3491117. XP002265131.

(Continued)

*Primary Examiner*—Margaret Einsmann
*Assistant Examiner*—Preeti Kumar

(57) ABSTRACT

This invention relates to antimicrobial polyester-containing articles and methodology for the preparation of antimicrobial polyester-containing articles utilizing chitosan and chitosan-metal complexes as the antimicrobial agent.

40 Claims, 20 Drawing Sheets

OTHER PUBLICATIONS

Chemical Abstracts Online, Honda, Kenji et al., Polymeric pyrrole derivatives. 9. Reactions between copper complexes containing pyrrole Schiff bases and 2,2-diphenyl-1-picrylhydrazyl, Database Accession No. 81:106212, XP002265132.

Chemical Abstracts Online, Tomono, Tsugikazu et al., Synthesis and polymerization of copper (II) and cobalt (III) complexes containing 3-(2-pyrrolylmethylenimino)prop-1-ene or p-(2-pyrrolylmethylenimino)styrene, Database accession No. 81:50107, XP002265133.

Gordon L. Eggleton et al., Oxygen-17 and Carbon-13 Nuclear Magnetic Resonance Spectra of Thiopene- and Pyrrole-2-carboxaldehyde. Condensation Products Prepared from Ephedrine Derivatives, Journal of Heterocyclic Chemistry, vol. 27(1853):1853-1855, 1990.

* cited by examiner

ANTIMICROBIAL POLYESTER-CONTAINING ARTICLES AND PROCESS FOR THEIR PREPARATION This application is a continuation-in-part of U.S. application Ser. No. 10/143,380, filed May 10, 2002 now abandoned (which is incorporated in its entirety as a part hereof), which claimed the benefit of U.S. Provisional Application No. 60/290,297, filed May 11, 2001.

FIELD OF THE INVENTION

This invention relates to antimicrobial polyester-containing articles and methodology for the preparation of antimicrobial polyester-containing articles utilizing chitosan and chitosan-metal complexes as the antimicrobial agent.

TECHNICAL BACKGROUND OF THE INVENTION

This invention relates to the use of chitosan and chitosan-metal complexes to generate polyester-containing articles having antimicrobial properties.

PCT application WO 00/49219 discloses the preparation of substrates with biocidal properties. The deposition of solubilized chitosan on polyester, among other materials, followed by treatment with silver salts, reduction of the silver salt and crosslinking the chitosan is disclosed to yield a durable biocidal article. The application also discloses the crosslinking of the chitosan after it is applied, either before or after the silver salt treatment.

JP Kokai H9-291478 discloses a process for the application of a chitosan derivative to polyester fabric comprising UV treatment of the polyester fabric followed by application of a chitosan-derived quaternary ammonium base. The UV irradiation serves to generate free radicals on the surface of the polyester fabric to which the chitosan is subsequently attached. H. Shin et al, *Sen-I Gakkaishi*, 54(8), 400–406 (1998) discloses similar UV fabric treatment and also a low temperature air plasma treatment prior to chitosan treatment.

JP Kokai H8-22772 discloses a process for the manufacture of an antibacterial acrylic yarn which comprises dipping, in an aqueous acidic chitosan solution, a wet spun yarn from an acrylonitrile-based polymer solution, neutralizing with an aqueous alkali solution, drying and densifying. The process may be carried out batch-wise or continuously. The chitosan is absorbed on the surface of the yarn and deposited in micro-voids within the yarn before drying.

S. Matsukawa et al., *Sen-I Gakkaishi*, 51(1), 51–56 (1995) disclose the modification of polyester fabrics using chitosan. The polyester was hydrolyzed with caustic soda, neutralized with 1% acetic acid solution, then treated with a chitosan solution and, optionally, with a crosslinking agent.

SUMMARY OF THE INVENTION

This invention provides an antimicrobial polyester-containing article having chitosan grafted onto the article and optionally, containing one or more metal salts, one or more carboxyl-containing polymers or combination thereof.

Further disclosed is a process for preparing antimicrobial polyester-containing articles comprising the sequential steps of:
(a) providing a polyester-containing article;
(b) contacting the polyester-containing article with a basic solution;
(c) optionally, washing the article produced in step (b);
(d) contacting the article produced in step (b) or step (c) with a strong mineral acid solution;
(e) optionally, washing the article produced in step (d);
(f) contacting the article produced in step (d) or step (e) with a solution comprising a chitosan agent selected from the group consisting of chitosan, chitosan salts and chistosan derivatives;
(g) optionally, heating the article produced in step (f);
(h) isolating the article produced in step (f) or step (g); and
(i) optionally, heating the article isolated in step (h) at a temperature higher than the temperature of step (g).

Further disclosed is a continuous process for producing an antimicrobial polyester-containing article comprising the sequential steps of:
(a) providing a feed station on which is disposed a polyester-containing article and a take-up station capable of receiving the polyester-containing article;
(b) drawing the article from the feed station through a first treatment station wherein said article is exposed to a basic solution;
(c) optionally drawing the step (b)-treated article through a second treatment station wherein the article is exposed to water;
(d) drawing the step (b)- or step (c)-treated article through a third treatment station wherein the article is exposed to a strong mineral acid solution;
(e) optionally, drawing the step (d)-treated article through a fourth treatment station wherein the article is exposed to deionized water;
(f) drawing the step (d)- or step (e)-treated article through a fifth treatment station wherein the article is exposed to a solution comprising a chitosan agent;
(g) optionally, heating the step (f)-treated article after it exits the chitosan treatment station; and
(h) causing the step (f)- or step (g)-treated article to be received on and accumulate on the take-up station.

DETAILED DESCRIPTION OF THE INVENTION

Figure 1:
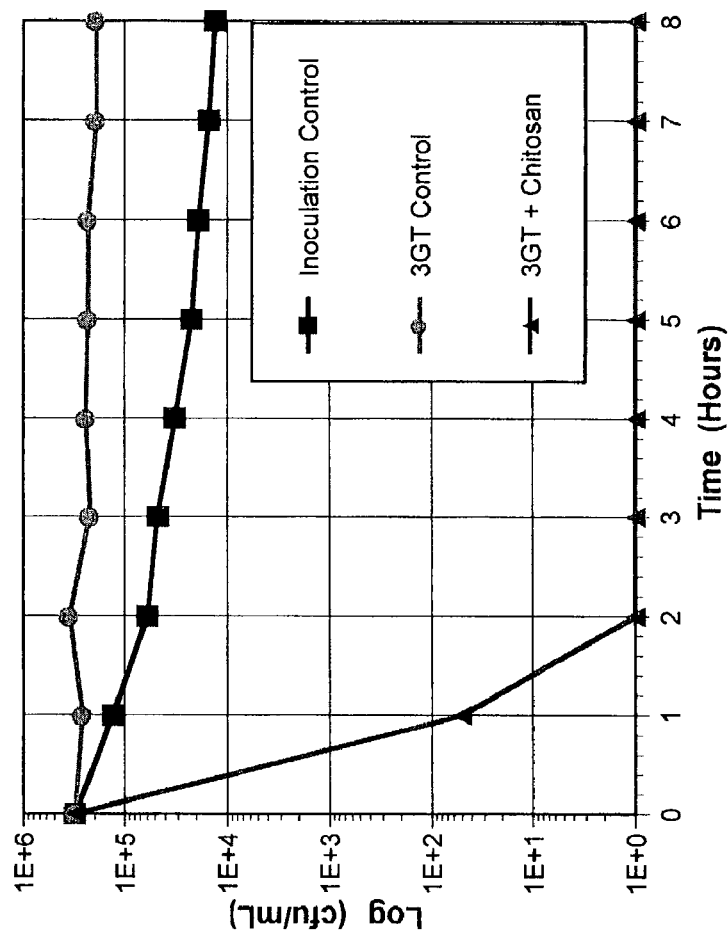
FIG. 1 is a diagram showing the antimicrobial effect of chitosan grafted on 3GT knit fabric vs. *Listeria monocytogenes* ATCC 15313.

The present invention involves the preparation of antimicrobial polyester-containing articles that have chitosan grafted thereon. Chitosan is the commonly used name for poly-[1-4]-β-D-glucosamine. Chitosan is chemically derived from chitin, which is a poly-[1-4]-β-N-acetyl-D-glucosamine which, in turn, is derived from the cell walls of fungi, the shells of insects and, especially, crustaceans. As used herein, the term "grafted" means that the chitosan is bound to the polyester substrate by either ionic (electrostatic) or covalent bonding. Grafting of the chitosan to the polyester article may be confirmed by Electron Spectroscopy for Chemical Analysis (ESCA) [see, for example, Xin Qu, Anders Wirsen, Bjorn Orlander, Anne-Christine Albertsson, Polymer Bulletin, (2001), vol. 46., pp. 223–229 and Huh, M. W., Kang, I., Lee, D. H., Kim, W. S., Lee, D. H., Park, L. S., Mln, K. E., and Seo, K. H., J. Appl. Polym. Sci. (2001), vol. 81, p. 2769]. Grafting is also established by the literature report of Ga-er Yu, Frederick G. Morin, Geffory A. R. Nobes, and Robert H. Marchessault, in Macromolecules, (1999), vol. 32, pp. 518–520). ESCA data demonstrate that the chitosan-modified surfaces of the polyester-containing articles of the present invention are similar in composition to those of the chitosan starting materials. The ESCA data also show that these surfaces have a significant level of nitrogen that is incorporated in a salt form, which provides evidence that the chitosan in physically linked to the surface through ionic interactions.

Polyesters comprise those polymers prepared from diols and dicarboxylic acids. Dicarboxylic acids useable in the preparation of polyesters include, but are not limited to, unsubstituted and substituted aromatic, aliphatic, unsaturated, and alicyclic dicarboxylic acids and the lower alkyl esters of dicarboxylic acids having from 2 carbons to 36 carbons. Specific examples of the desirable dicarboxylic acid component include terephthalic acid, dimethyl terephthalate, isophthalic acid, dimethyl isophthalate, 2,6-napthalene dicarboxylic acid, dimethyl-2,6-naphthalate, 2,7-naphthalenedicarboxylic acid, dimethyl-2,7-naphthalate, 3,4'-diphenyl ether dicarboxylic acid, dimethyl-3,4'diphenyl ether dicarboxylate, 4,4'-diphenyl ether dicarboxylic acid, dimethyl-4,4'-diphenyl ether dicarboxylate, 3,4'-diphenyl sulfide dicarboxylic acid, dimethyl-3,4'-diphenyl sulfide dicarboxylate, 4,4'-diphenyl sulfide dicarboxylic acid, dimethyl-4,4'-diphenyl sulfide dicarboxylate, 3,4'-diphenyl sulfone dicarboxylic acid, dimethyl-3,4'-diphenyl sulfone dicarboxylate, 4,4'-diphenyl sulfone dicarboxylic acid, dimethyl-4,4'-diphenyl sulfone dicarboxylate, 3,4'-benzophenonedicarboxylic acid, dimethyl-3,4'-benzophenonedicarboxylate, 4,4'-benzophenonedicarboxylic acid, dimethyl-4, 4'-benzophenonedicarboxylate, 1,4-naphthalene dicarboxylic acid, dimethyl-1,4-naphthalate, 4,4'-methylene bis(benzoic acid), dimethyl-4,4'-methylenebis(benzoate), oxalic acid, dimethyl oxalate, malonic acid, dimethyl malonate, succinic acid, dimethyl succinate, methylsuccinic acid, glutaric acid, dimethyl glutarate, 2-methylglutaric acid, 3-methylglutaric acid, adipic acid, dimethyl adipate, 3-methyladipic acid, 2,2,5,5-tetramethylhexanedioic acid, pimelic acid, suberic acid, azelaic acid, dimethyl azelate, sebacic acid, 1,1 1-undecanedicarboxylic acid, 1,10-decanedicarboxylic acid, undecanedioic acid, 1,12-dodecanedicarboxylic acid, hexadecanedioic acid, docosanedioic acid, tetracosanedioic acid, dimer acid, 1,4-cyclohexanedicarboxylic acid, dimethyl-1,4-cyclohexanedicarboxylate, 1,3-cyclohexanedicarboxylic acid, dimethyl-1,3-cyclohexanedicarboxylate, 1,1-cyclohexanediacetic acid, metal salts of 5-sulfo-dimethylisophalate, fumaric acid, maleic anhydride, maleic acid, hexahydrophthalic acid, phthalic acid and the like and mixtures derived therefrom.

Diols useful in the preparation of polyesters include, but are not limited to, unsubstituted, substituted, straight chain, branched, cyclic aliphatic, aliphatic-aromatic or aromatic diols having from 2 carbon atoms to 36 carbon atoms. Specific examples of the desirable diol component include ethylene glycol, 1,3-propanediol, 1,2-propanediol, 1,2-, 1,3- and 1,4-butanediol, 1,5-pentane diol, 1,6-hexanediol, 1,8-octanediol, 1,10-decanediol, 1,12-dodecanediol, 1,14-tetradecanediol, 1,16-hexadecanediol, dimer diol, isosorbide, 4,8-bis (hydroxymethyl)-tricyclo [5.2.1.0/2.6]decane, 1,2-, 1,3- and 1,4-cyclohexanedimethanol, and the longer chain diols and polyols made by the reaction product of diols or polyols with alkylene oxides including di(ethylene glycol), tri(ethylene glycol), poly(ethylene ether) glycols, poly(butylene ether) glycols and the like and mixtures derived therefrom.

The preferred polyesters useful herein are poly(ethylene terephthalate) ("2GT"), poly(trimethylene terephthalate) ("3GT"), and blends and copolymers thereof.

The term "polyester-containing article" as used herein means an article that has a surface composition of at least 10% polyester by area.

In apparel applications, garments comprising polyester often include other components, such as acrylic, wool, silk, cotton, linen, flax, hemp, rayon, cellulose, wood pulp, cellulose acetate or triacetate, nylon 6 or nylon 66, poly(m-phenylene isophthalamide) ('PMIA,' available from E. I. du Pont de Nemours and Company, Wilmington, Del., U.S.A. under the trademark Nomex®), poly(p-phenylene terephthalamide) ('PPTA,' available from E. I. du Pont de Nemours and Company under the trademark Kevlar®), polyolefins such as polypropylene and polyethylene, fiberglass, Lycra® spandex (available from E. I. du Pont de Nemours and Company), and elastomers. Polyesters other than poly(ethylene terephthalate) may also be present, for example, a copolymer with a low melt temperature that is used as a binder fiber in fiberfill.

Combination of the fibers listed above can be used in the present invention for added benefits. Such fiber combinations can be prepared by any means known to those skilled in the art. "Bicomponent" filaments in which two polymers are arranged side-by-side or in a sheath-core arrangement can be formed during the spinning process. 2GT/3GT bicomponent fibers such as are disclosed in U.S. Pat. No. 3,671,379, herein incorporated by reference, are one example useful in the present invention.

Another means of preparing fiber combinations is by intimate blending of staple fibers; i.e., as the staple yarn is spun, the different fibers can be combined in either a carding or drawing process. Fiber combinations can also be prepared by knitting or weaving yarns, staple, or filament of different composition into the same fabric. In the case of Lycra® spandex (E. I. de Nemours and Company, Wilmington, Del.), the spandex is added in staple yarn at either the spinning step or during fabric production, such as plating in knitting.

As a first step of the process of the present invention, polyester-containing articles are pretreated. This pretreatment involves hydrolyzing the surface of said polyester-containing article to prepare it for subsequent attachment of chitosan groups. The pretreatment is achieved by the hydrolytic rupture of some of the ester bonds in the polyester-containing articles to generate carboxylate groups.

The hydrolysis treatment involves exposure of the polyester-containing article to an aqueous solution of a base. All soluble Group I, II, and III hydroxides, ammonium hydroxide, and alkyl-substituted ammonium hydroxides can be used to effect hydrolysis. The base can be dissolved in water or a mixture of water with one or more water-soluble organic solvents. Examples of suitable water-soluble organic solvents include methanol, ethanol, propanol, ethylene glycol, propylene glycol, acetonitrile, dimethylformamide, and dimethylacetamide.

The base useful in the invention is typically an alkali metal hydroxide, most preferably sodium hydroxide. The concentration of base in the aqueous solution is not critical and depends on the base being used and the treatment temperature. In the case of sodium hydroxide, the concentration may range from 1 to 40% by weight. The temperature of the treatment is not critical, room temperature being preferred. Temperature ranges of 10 to 90° C. may be employed. Lower temperature is preferred with the higher concentrations of base. The article is exposed to the basic solution long enough to reduce its weight by from 1 to 30 percent, preferably by from 1 to 10 percent. The treatment time will depend on the concentration and temperature of the basic solution; the higher the concentration of the base solution, and the higher the temperature employed the shorter the time of treatment. Times as low as 2 to 30 seconds can be employed successfully. Optionally, the article is then washed with water to remove the bulk of the base solution.

Following the hydrolysis treatment, the article is acidified by treatment with strong mineral acid to a pH of less than or equal to the pKa of the carboxylate groups generated by the hydrolysis treatment. The article can be directly acidified with aqueous mineral or organic acids without the involvement of water washing. However, aqueous washing is preferred to minimize the use of acids. As used herein, the term "strong" mineral acid, means acids having a pH less than pH 2. Mineral acids useful herein include, for example, hydrochloric, sulfuric and phosphoric acids. Hydrochloric acid is most preferred. The time and temperature of the acidification step are not critical; times ranging from 2 seconds to 30 minutes at room temperature can be employed successfully.

Optionally, the article is again washed with water to remove the bulk of the mineral acid. The article may then be used directly in the next step, or may, optionally, be dried.

While not desiring to be bound by any particular theory, it is believed that the acidification below the pKa of the carboxylate groups, resulting in the formation of the free carboxylic acid group, greatly increases the rate and efficacy of the reaction of the carboxyl species with chitosan in the subsequent step.

Following the acidification step, the article is treated with chitosan. This comprises soaking or wetting the article with a solution containing a chitosan agent. The term "chitosan agent" as used herein means all chitosan-based moieties, including chitosan, chitosan salt, and chitosan derivatives. The solution comprising the chitosan agent may be aqueous. However, since chitosan by itself is not soluble in water, the chitosan may be solubilized in a solution. Solubility is obtained by adding the chitosan to a dilute solution of a water-soluble, organic acid selected from the group consisting of mono-, di- and polycarboxylic acids. This allows the chitosan to react with the acid to form a water-soluble salt, herein referred to as "chitosan salt." Alternatively, "chitosan derivatives," including N- and O-carboxyalkyl chitosan, that are water-soluble, can be used directly in water instead of chitosan salt. . The chitosan may also be dissolved in special solvents like dimethylacetamide in the presence of lithium chloride, or N-methyl-morpholine-N-oxide. Such solubilized chitosan solutions can be used in the present invention instead of aqueous solutions containing chitosan salt or chitosan derivatives.

Typically, the chitosan solution is an aqueous acetic acid solution, for example, an aqueous solution containing 2% chitosan and 0.75% acetic acid or 2% chitosan and 1.5% aqueous acetic acid. The time of treatment is typically 5 to 30 minutes. The temperature of the treatment is not critical, room temperature being preferred. After treatment with chitosan solution, excess solution may be allowed to drip out, or may be removed by wringing or spinning.

Optionally, the treated article is then dried via oven drying or a combination of ambient air drying and oven drying.

Articles prepared by the above methods exhibit antimicrobial properties. The term "antimicrobial" as used herein, means both bactericidal and fungicidal. In addition, the fibers and yarns processed herein exhibit favorable physical properties with respect to tenacity, elongation and hand-feel.

Said antimicrobial properties may, optionally, be further enhanced by treatment with soluble metal salts, for example, soluble silver salts, soluble copper salts and soluble zinc salts. The preferred metal salts of the invention are aqueous solutions of zinc sulfate, copper sulfate or silver nitrate. The metal salts are typically applied by dipping or padding a dilute (0.1 to 5%) solution of salt in water. The degree of enhancement depends on the particular metal salt used, its concentration, the time and temperature of exposure, and the specific chitosan treatment, that is, the type of chitosan agent, its concentration, the temperature, and the time of exposure. Examples 3, 4, 5, 6 and 7; FIGS. 7, 8, 9, 10 and 11; and Table 1 demonstrate the effect of metal salts in the process of the invention.

Articles prepared by the above method of the invention also exhibit improved antistatic properties. Antistatic properties refer to the ability of a textile material to disperse an electrostatic charge and to prevent the buildup of static electricity. (*Dictionary of Fiber & Textile Technology*, Hoechst Celanese Corp., Charlotte, N.C. (1990), p. 8)

A further optional post-treatment comprises applying a carboxyl-containing polymer to the chitosan treated article, or to the metal salt treated chitosan treated article. The term "carboxyl-containing polymer" as used herein means a polymer that contains carboxylic acid groups in side chains attached to the polymer backbone. The carboxyl-containing polymer, most preferably polyacrylic acid, is typically applied from a dilute aqueous solution by dipping or padding.

Any of the above described chitosan-treated articles, metal salt-treated articles or the carboxyl-containing polymer-treated articles, may benefit from a further chitosan solution treatment. Included within the scope of this invention are articles that, having received a first treatment with chitosan by the process of the present invention, are further subjected to one or more treatments with metal salt, carboxyl-containing polymer and/or additional chitosan in any order, with the proviso that the surface of the final article is treated with metal salt or a chitosan solution.

In a preferred embodiment, the process of the invention further involves heating the chitosan-grafted polyester-containing article to a temperature of from 35° C. to 190° C. under a nitrogen or ambient atmosphere for from 30 seconds to 20 hours, washing with deionized water and further drying the article at a temperature of 35° C. to 190° C. for from 30 seconds to 20 hours.

Figure 20:
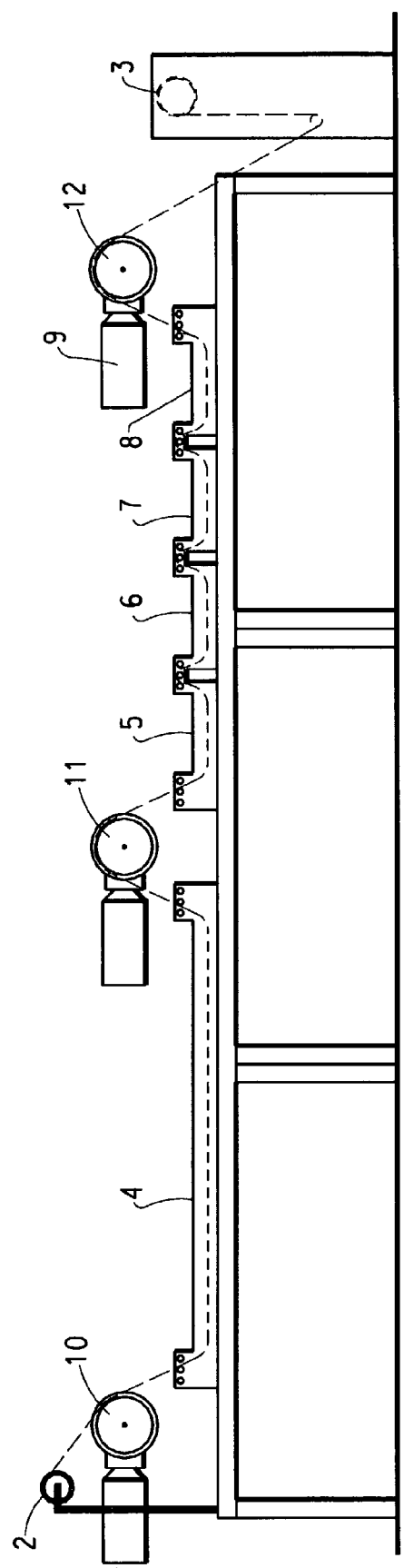
FIG. 20 is a schematic diagram of the continuous process of the invention for making antimicrobial polyester-containing articles.

The articles of the present invention can also be produced in a continuous process. The process is illustrated by FIG. 20 of the drawings herein. Referring now to FIG. 20, there is shown an apparatus for performing the following sequential steps of the invention:

(a) A feed station (2) on which is disposed a polyester-containing article (1) is provided. The feed station would typically comprise one or more feed rollers (10).

(b) The article is drawn from the feed station through a first treatment station (4) wherein said article is exposed to a basic solution. The treatment stations herein would typically be immersion bath trays or tanks.

(c) The article is optionally drawn from the first treatment station through a second treatment station (5) wherein the step (b)-treated article is exposed to water. Optionally, one or any number of draw rolls (11) may help guide the article between the treatment stations. Draw rolls such as draw roll (11) may be placed along any step of the continuous process as is commonly known in the art.

(d) The article from the second treatment station is drawn through a third treatment station (6) wherein the step (c)-treated article is exposed to a strong mineral acid solution.

(e) Optionally, the article from the third treatment station is drawn through a fourth treatment station (7) wherein the step (d)-treated article is exposed to water.

(f) The article is then drawn through a fifth treatment station (8) wherein the step (d)- or step (e)-treated article is exposed to a solution comprising the chitosan agent. As discussed above, the chitosan agent is selected from the group consisting of chitosan, chitosan salts and chitosan derivatives. The treatment stations would typically be immersion bath trays or tanks.

(g) Optionally, the step (f)-treated article is heated by a heater, such as a heater roll assembly (9) after it exits the chitosan treatment station. (h) The step (f)- or step (g)-treated article is then received on and accumulates on the take-up station (3). The treated article would typically be wound by means of a traversing guide (12) onto the take-up station (3) which is typically one or more cardboard or resin tubes to form spinning bobbins.

The feed station, treatment stations, heaters, and take-up components may be any convenient means known in the art for continuous treatment of fibers and yarns (see, for example, *Ullmann's Encyclopedia of Industrial Chemistry*, fifth Edition, Wolfgang Gerhartz, Executive Editor, Volume A10, VCH Verlagsgesellschaftg, Weinheim, Federal Republic of Germany (1987), "Fibers, 3. General Production Technology," H. Lucker, W. Kagi, U. Kemp, and W. Stibal, pp. 511–566). The continuous process is particularly appropriate for treating polyester-containing fiber or yarn on a commercial scale.

The process and articles of the present invention do not employ crosslinking agents which makes the process more efficient and economical than other currently available processes requiring the use of crosslinking agents. The phrase "crosslinking agent" connotes the commonly used di- or tri-functional crosslinking agents known in the art. The carboxyl-containing polymers, e.g. polyacrylic acids, are not construed to be crosslinking agents in the context of the present invention.

The preferred articles of the present invention are in the form of fibers; fabrics, including wovens and nonwovens; filaments; films; and articles and constructs prepared therefrom.

The antimicrobial articles of the invention shall find application in uses such as apparel, including sportswear, activewear, intimate apparel, swimwear and medical garments; healthcare, including medical drapes, antimicrobial wipes, surfaces (counters, floors, walls), personal hygiene products and medical packaging; household articles, including fiberfill, bedding, window treatments and surfaces; and food processing/service, including packaging, absorbent antimicrobial pads for meat packaging, antimicrobial wipes and surfaces.

EXAMPLES

Materials and Methods

The following fiber-based materials were used in the following Examples. Woven and knit fabrics were also tested as outlined in the Examples.

1. Poly(ethylene terephthalate) ("2GT") fiber, knit fabric and microfiber woven fabric, from E. I. du Pont de Nemours and Company (Wilmington, Del.).

2. Sorona® poly(trimethylene terephthalate) ("3GT") yarn, 70 denier, 34 filament, round cross-section, made by E. I. du Pont de Nemours and Company (Wilmington, Del.).

The chitosan materials used in this study were obtained as commercially available from Primex Ingredients ASA, Norway under the trademark Chitoclear® chitosan and were used as purchased.

All Examples demonstrate the use of chitosan salt, i.e., chitosan dissolved in acetic acid as the chitosan agent of the invention.

Treated articles were tested for antimicrobial properties by the Shake Flask Test for Antimicrobial Testing of Materials, as follows:
1. A single, isolated colony from a bacterial or yeast agar plate culture was inoculated in 15–25 ml of Trypticase Soy Broth (TSB) in a sterile flask. It was incubated at 25–37° C. (using optimal growth temperature for the specific microbe) for 16–24 hours with or without shaking (selecting appropriate aeration of the specific strain). For filamentous fungi, sporulating cultures were prepared on agar plates.
2. The overnight bacterial or yeast culture was diluted into sterile phosphate buffer (see below) at pH 6.0 to 7.0 to obtain approximately $10^5$ colony forming units per ml (cfu/ml). The total volume of phosphate buffer needed was 50 ml×number of test flasks (including controls). For filamentous fungi, spore suspensions at $10^5$ spores/ml were prepared. Spore suspensions were prepared by gently resuspending spores from an agar plate culture that had been flooded with sterile saline or phosphate buffer. To obtain initial inoculum counts, final dilutions (prepared in phosphate buffer) of $10^{-4}$ and $10^{-3}$ were plated onto Trypticase Soy Agar (TSA) plates in duplicate. Plates were incubated at 25–37° C. overnight.
3. 50 ml of inoculated phosphate buffer was transferred into each sterile test flask containing 0.5 g of material to be tested. Also, control flasks of inoculated phosphate buffer and uninoculated phosphate buffer with no test materials were prepared.
4. All flasks were placed on a wrist-action shaker and incubated with vigorous shaking at room temperature. All flasks were sampled periodically and appropriate dilutions were plated onto TSA plates. The TSA plates were incubated at 25–37° C. for 16–48 hours and colonies were then counted.
5. Colony counts were reported as the number of Colony Forming Units per ml (cfu/ml).
6. The activity constant, At value, was calculated as follows: $\Delta t = C - B$, where $\Delta t$ is the activity constant for contact time t, C is the mean $\log_{10}$ density of microbes in flasks of untreated control materials after X hours of incubation, and B is the mean $\log_{10}$ density of microbes in flasks of treated materials after X hours of incubation. $\Delta t$ was typically calculated at 4, 6, or 24 hours and may be expressed as $\Delta t_X$.

Stock phosphate buffer:
Monobasic Potassium Phosphate 22.4 g
Dibasic Potassium Phosphate 56.0 g
Deionized Water volume increased to 1000 ml The pH of the phosphate buffer was adjusted to pH 6.0 to 7.0 with either NaOH or HCl. The stock phosphate buffer was filtered, sterilized, and stored at 4° C. until use. The working phosphate buffer was prepared by diluting 1 ml of stock phosphate buffer in 800 ml of sterile deionized water.

Example 1

Preparation of Chitosan Grafted 2GT and 3GT Knit Standard Polyester Fabrics

Polyester fabrics (8 inch×9 inch; 3GT fabric weighing 21.8 g, 2GT fabric weighing 19.5 g) were soaked in 10% aqueous sodium hydroxide solution and gently shaken for 90 min. Each was then washed with water and soaked in 1 M aqueous hydrochloric acid solution for 30 min, washed with deionized water and dried in air for 1 h. Each was then immersed in 2 weight % aqueous chitosan solution (mol. wt. 75,000,) containing 1.5% acetic acid for 30 min, The chitosan used in Example 1 was food grade Chitoclear® chitosan (Primex Ingredients ASA, Norway). The degree of N-deacetylation of this sample was over 90% and this was ascertained by proton and carbon 13 NMR spectroscopy. The molecular weight of this sample was estimated using standard relative viscosity measurements as reported in the literature. The excess chitosan was allowed to drip, air dried for an hour and then dried at 85° C. for 16 h under nitrogen atmosphere. The weights of the chitosan-grafted fabrics were: 3GT, 24.06 g; 2GT, 21.32 g. The fabrics were then washed with water and dried at 80° C. for 16 h to give a 3GT sample weighing 23.3 g and a 2GT sample weighing 20.6 g (6.8 and 5.6% chitosan incorporation, respectively). These fabrics were tested for their antimicrobial efficacy as described above.

Figure 2:
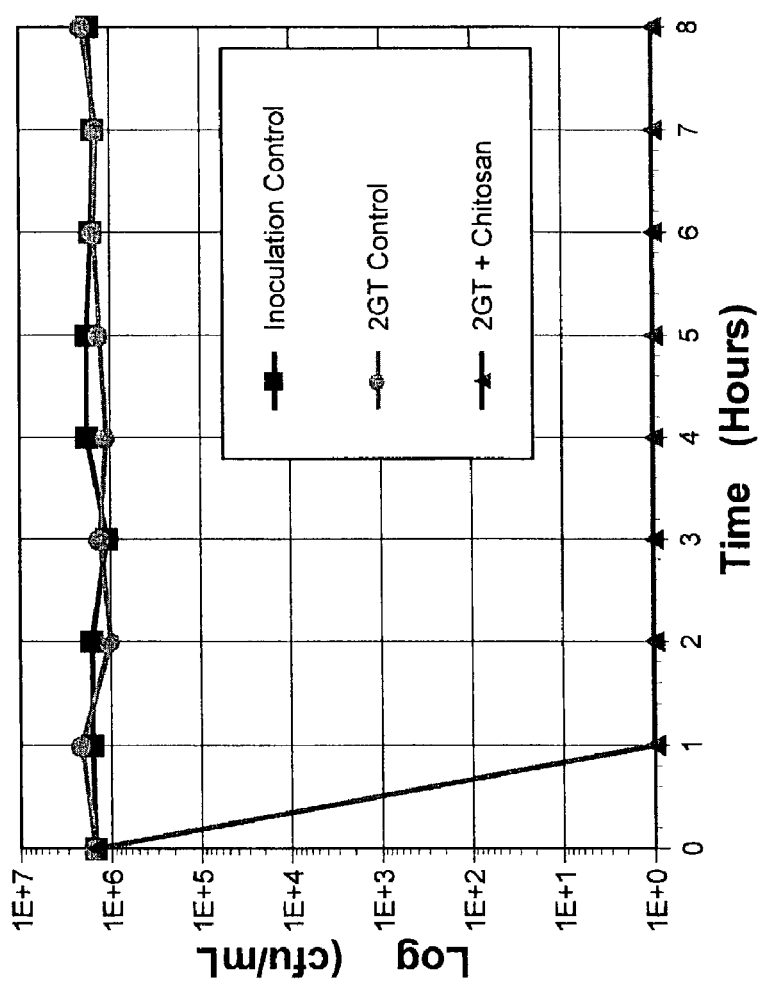
FIG. 2 is a diagram showing the antimicrobial effect of chitosan grafted on 2GT knit fabric vs. *Klebsiella pneumoniae* ATCC 4352.
Figure 3:
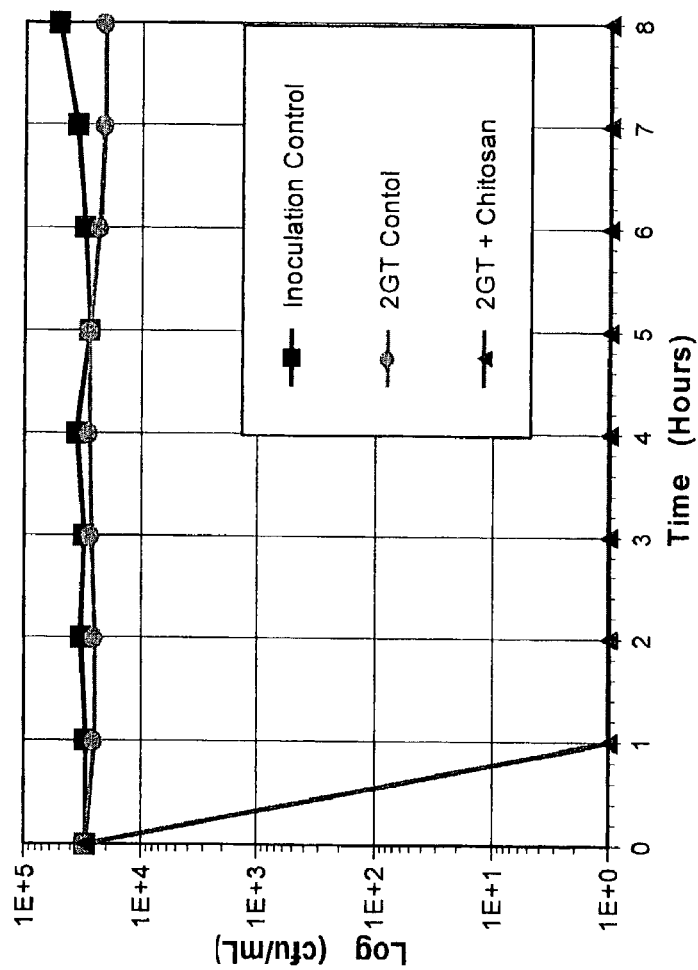
FIG. 3 is a diagram showing the antimicrobial effect of chitosan grafted on 2GT knit fabric vs. *Candida albicans* ATCC 10231.
Figure 4:
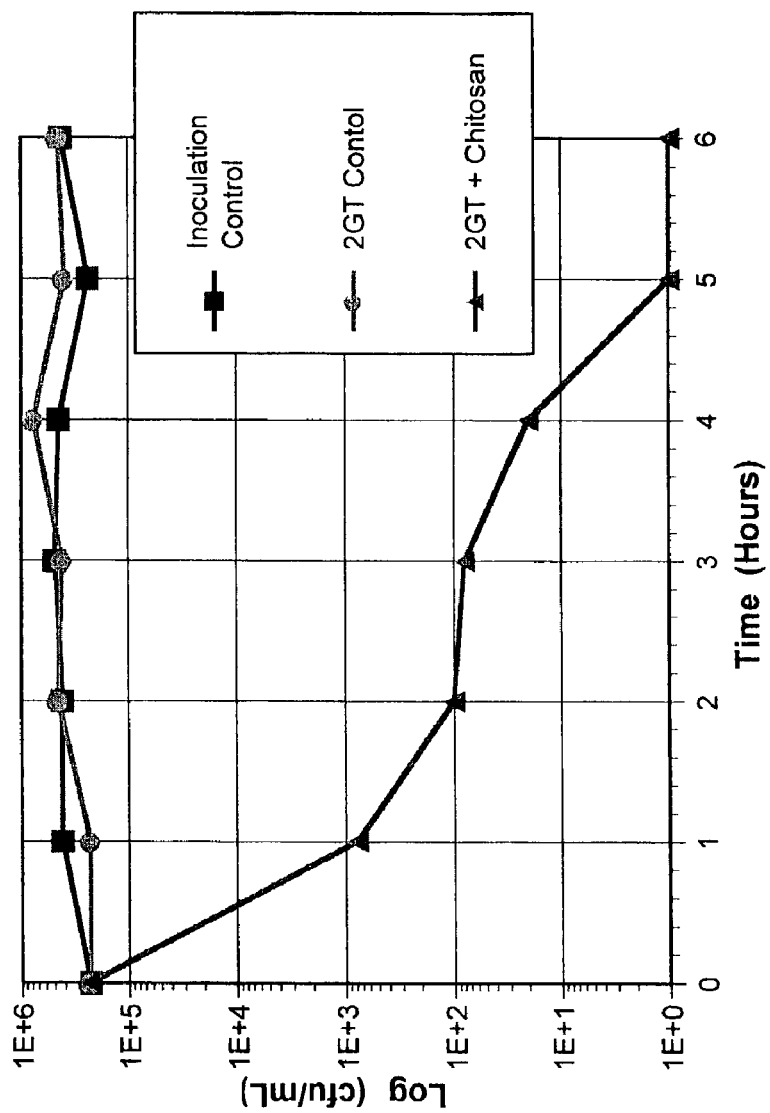
FIG. 4 is a diagram showing the antimicrobial effect of chitosan grafted on 3GT woven fabric vs. *Staphylococcus aureus* ATCC 6538.

FIG. 1 shows the antimicrobial effect of chitosan grafted on 3GT knit fabric vs. *Listeria monocytogenes* ATCC 15313; the 3GT control is untreated fabric. FIG. 2 shows the antimicrobial effect of chitosan grafted on 2GT knit fabric vs. *Klebsiella pneumoniae* ATCC 4352; the 2GT control is untreated fabric. FIG. 3 shows the antimicrobial effect of chitosan grafted on 2GT knit fabric vs. *Candida albicans* ATCC 10231. FIG. 4 shows the antimicrobial effect of chitosan grafted on 3GT woven fabric vs. *Staphylococcus aureus* ATCC 6538.

Chitosan grafted onto 2GT and 3GT polyester fabrics demonstrated at least a 3-log reduction of the following microorganisms in 4–6 h:
*Escherichia coli* ATCC 25922
*Escherichia coli* ATCC 49106 (enterotoxigenic/enterohemorrhagic)
*Escherichia coli* O157:H7 (enterotoxigenic/enterohemorrhagic)
*Salmonella cholerasuis* ATCC 9239
*Staphylococcus aureus* ATCC 6538
*Bacillus subtilis* ATCC 6633
*Enterococcus faecalis* ATCC 29212
*Klebsiella pneumoniae* ATCC 4352
*Listeria monocytogenes* ATCC 15313
*Listeria welshimeri* ATCC 35897
*Pseudomonas aeruginosa* ATCC 27853
*Candida albicans* ATCC 10231
*Acinetobacter* sp. ATCC 14291
*Micrococcus luteus* ATCC 4698
*Staphylococcus cohnii* ATCC 49330
*Staphylococcus hominus* ATCC 27844

Example 2

Figure 5:
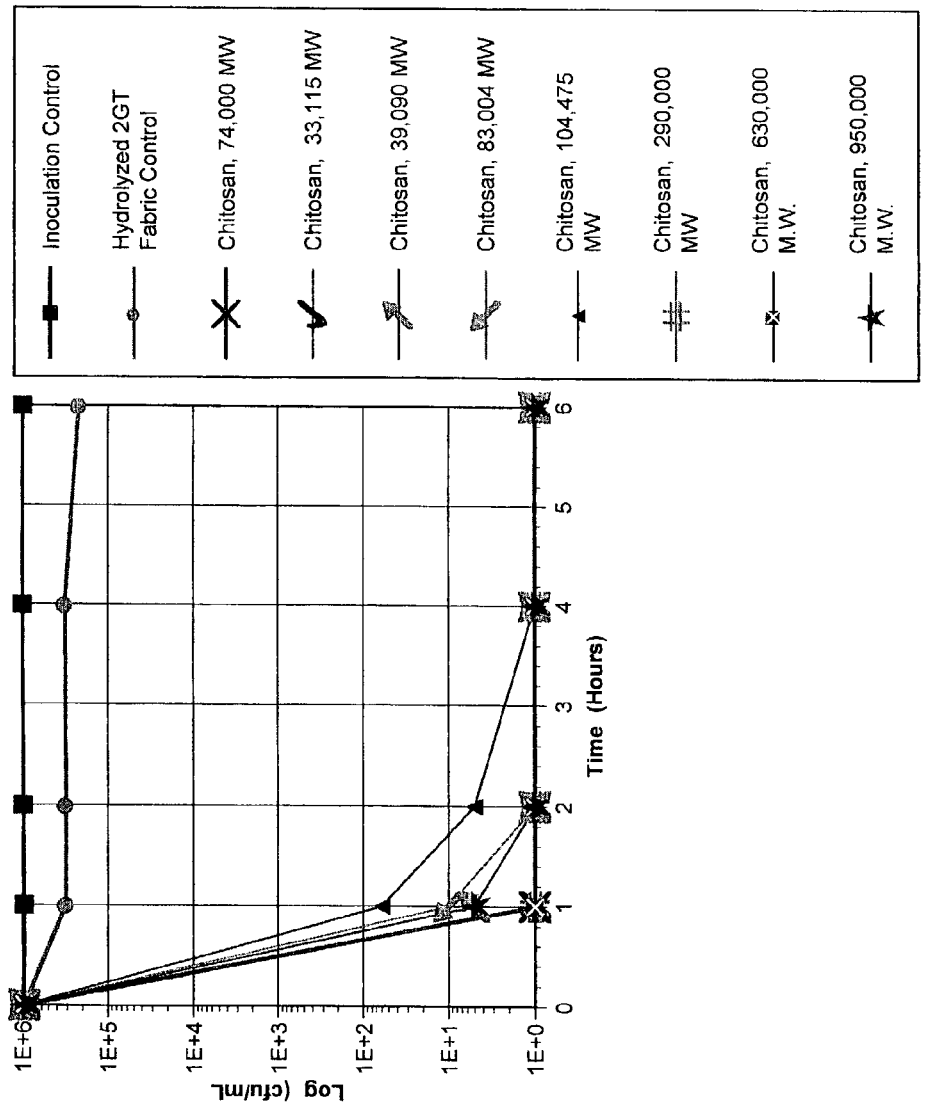
FIG. 5 is a diagram showing the antimicrobial effect of chitosans of various molecular weights grafted onto 2GT woven microfiber fabric vs. *E. coli* ATCC 25922.
Figure 6:
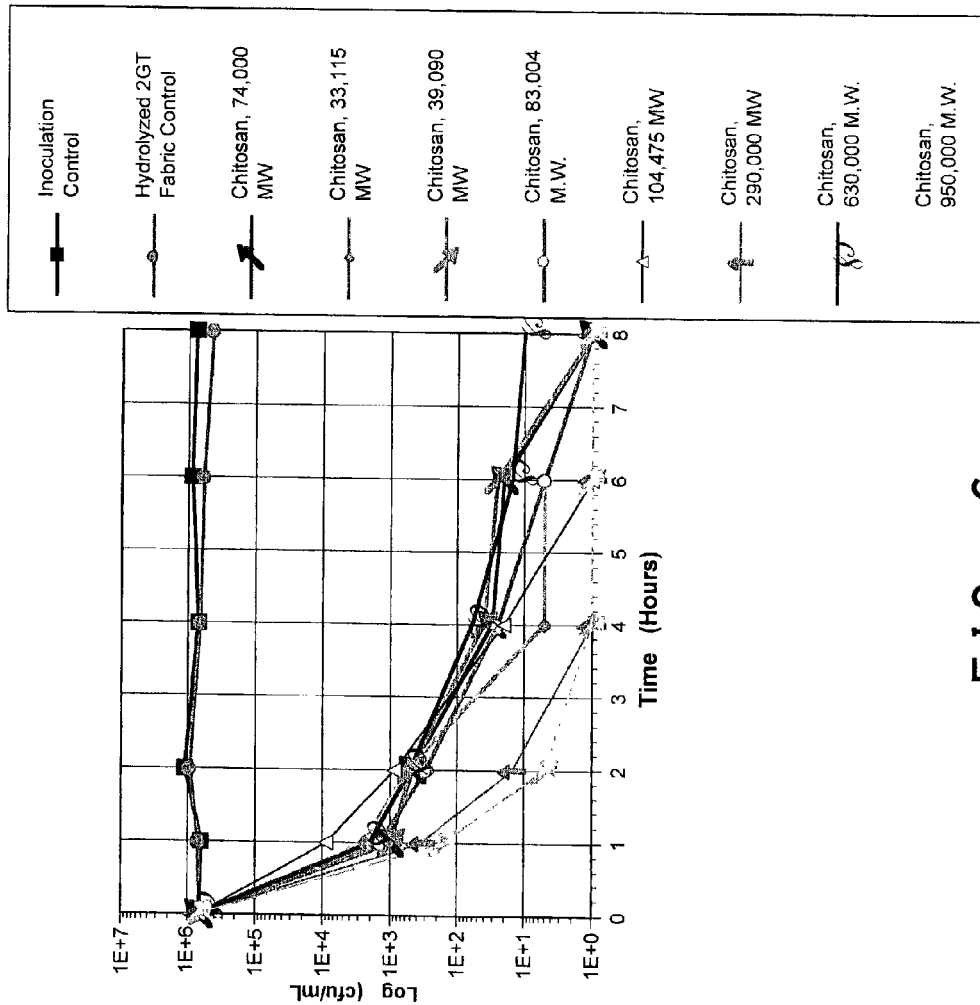
FIG. 6 is a diagram showing the antimicrobial effect of chitosans of various molecular weights grafted onto 2GT woven microfiber fabric vs. *Staphylococcus aureus* ATCC 29213.

Grafting of Chitosan Samples of Varying Molecular Weight onto 2GT Fabrics and the Evaluation of the Resulting Antimicrobial Properties Chitosan samples with degree of de-N-acetylation of over 80% and mol. wt. in the range of 950,000 (Pfansteihl, U.S.A.), 630,000 (Sigma Chemical Company, U.S.A.), 290,000 (Kitomer, Canada), 104,000 (Chitoclear®, industrial grade, Primex Ingredients ASA, Norway), 83,000 (Chitoclear®, industrial grade, Primex Ingredients ASA, Norway), 74,000 (Chitoclear®, food grade, Primex Ingredients ASA, Norway), 39,000 (Chitoclear®, food grade, Primex Ingredients ASA, Norway), and 33,000 (Chitoclear®, food grade, Primex Ingredients ASA, Norway) were grafted onto polyester fabrics in order to evaluate the effect of chitosan molecular weight on the antimicrobial activity. A 1% solution of each commercial chitosan in 0.75% aqueous acetic acid was used in the grafting procedure as described in Example 1. As shown in FIG. 5 (2GT; *E. coli* ATCC 25922) and FIG. 6 (2GT; *Staphylococcus aureus* ATCC 29213), the process of this invention is operable with chitosans of a wide range of molecular weights.

Example 3

Preparation of Chitosan Grafted Fabrics Treated With Antimicrobial Salts

Chitosan grafted 3GT woven fabric (22.8 g), prepared according to the procedure of Example 1 was soaked in 2% aqueous silver nitrate solution for 30 min, extensively washed with water, and dried at 37° C. for 16 h. Weight of the resultant fabric was 23.0 g.

Similarly, chitosan grafted 3GT knit fabric (23.1 g), prepared according to the procedure of Example 1 was treated with 2% copper sulfate solution as described above to obtained copper doped fabric, (23.7 g).

Figure 7:
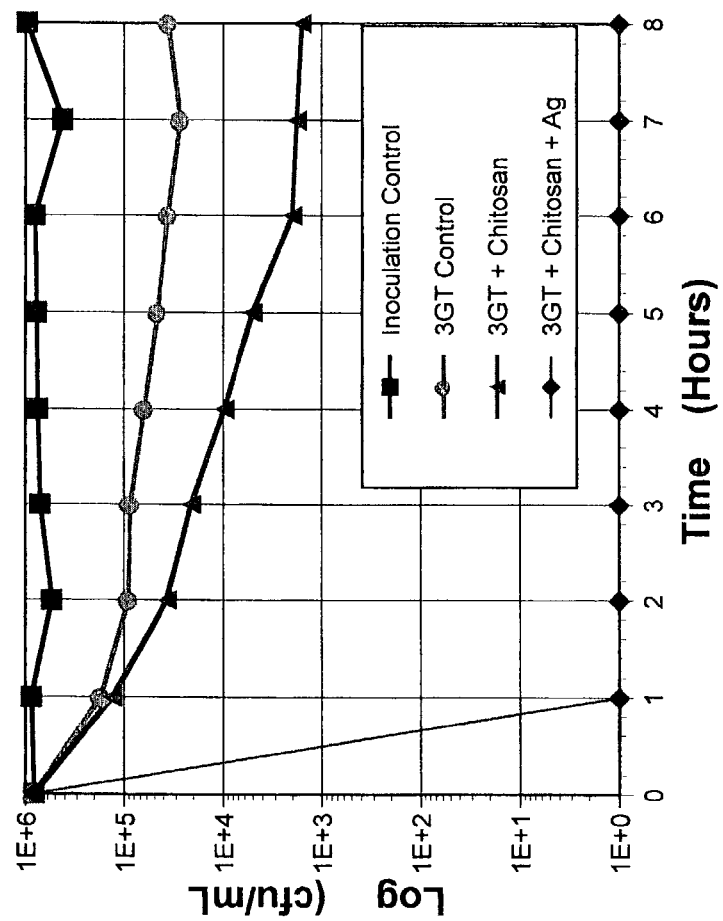
FIG. 7 is a diagram showing the antimicrobial effect of chitosan grafted onto 3GT fabrics with and without silver nitrate treatment vs. *Salmonella cholerasuis* ATCC 9239.
Figure 8:
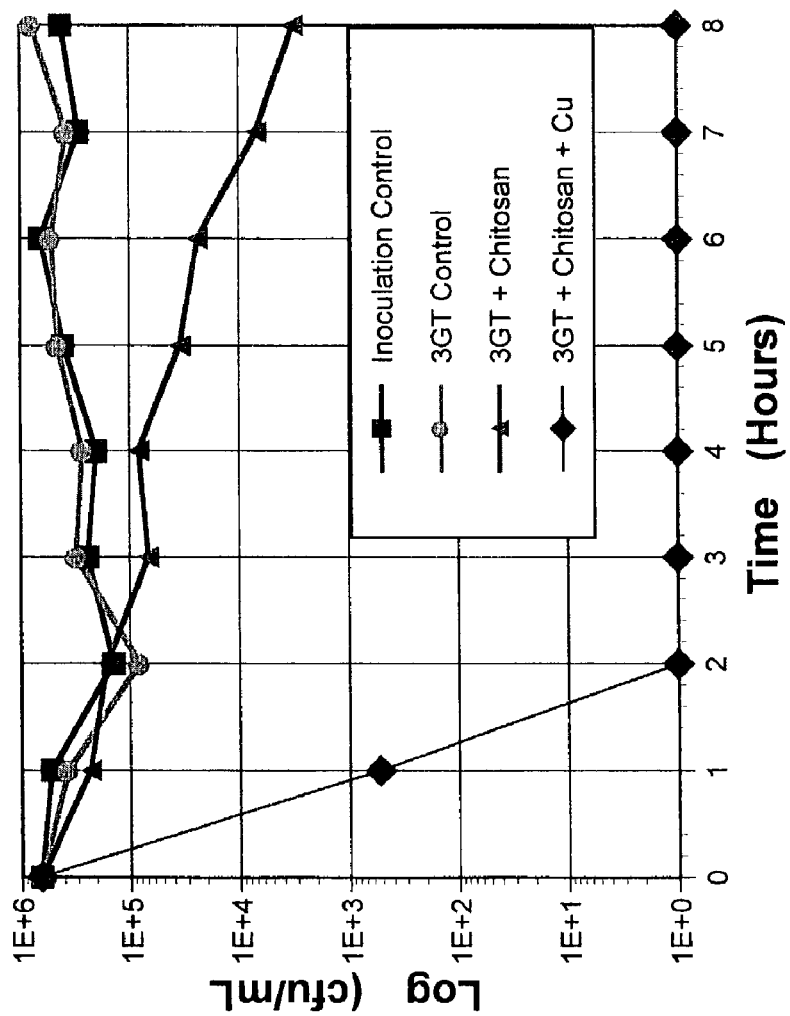
FIG. 8 is a diagram showing the antimicrobial effect of chitosan grafted on 3GT fabrics with and without copper sulfate treatment vs. *E. coli* O157:H7.

As indicated by the results obtained, metal doping of chitosan-grafted polyester may be used to enhance antimicrobial activity. Silver nitrate (FIG. 7), copper sulfate (FIG. 8) or, by a similar procedure, zinc sulfate were used successfully as metal dopes. FIG. 7 demonstrates 3GT fabrics prepared with grafted chitosan with or without a silver nitrate dope vs. *Salmonella cholerasuis* ATCC 9239. FIG. 8 demonstrates 3GT fabrics prepared with grafted chitosan with or without a copper sulfate dope vs. *E. coli* O157:H7.

Chitosan grafted onto 2GT and 3GT polyester, followed by doping with metals has demonstrated at least a 3-log reduction of the following microorganisms, which are known to be more resistant to antimicrobials, in 4–6 h:

*Escherichia coli* ATCC 49106 (enterotoxigenic/enterohemorrhagic)
*Escherichia coli* O157: H7 (enterotoxigenic/enterohemorrhagic)
*Salmonella cholerasuis* ATCC 9239

Example 4

Preparation of Chitosan Grafted Fabrics After Treated With Various Concentrations of Silver Nitrate Solution 2GT knit fabrics in the form of (five) socks were soaked in water, the excess water drained, and then treated with 40% aqueous sodium hydroxide for 2 min. These socks were then extensively washed with water and soaked in 1M aqueous hydrochloric acid for 2 min, then washed with water. This was followed by immersing the socks in aqueous 1% chitosan (Chitoclear®, food grade, mol. wt. 74,000, Primex Ingredients ASA, Norway) solution containing 0.75% acetic acid for 2 min, then excess solution allowed to drain followed by drying the socks at 85° C. for 16 h under nitrogen. These dried samples were washed again with water and re-dried.

Figure 9:
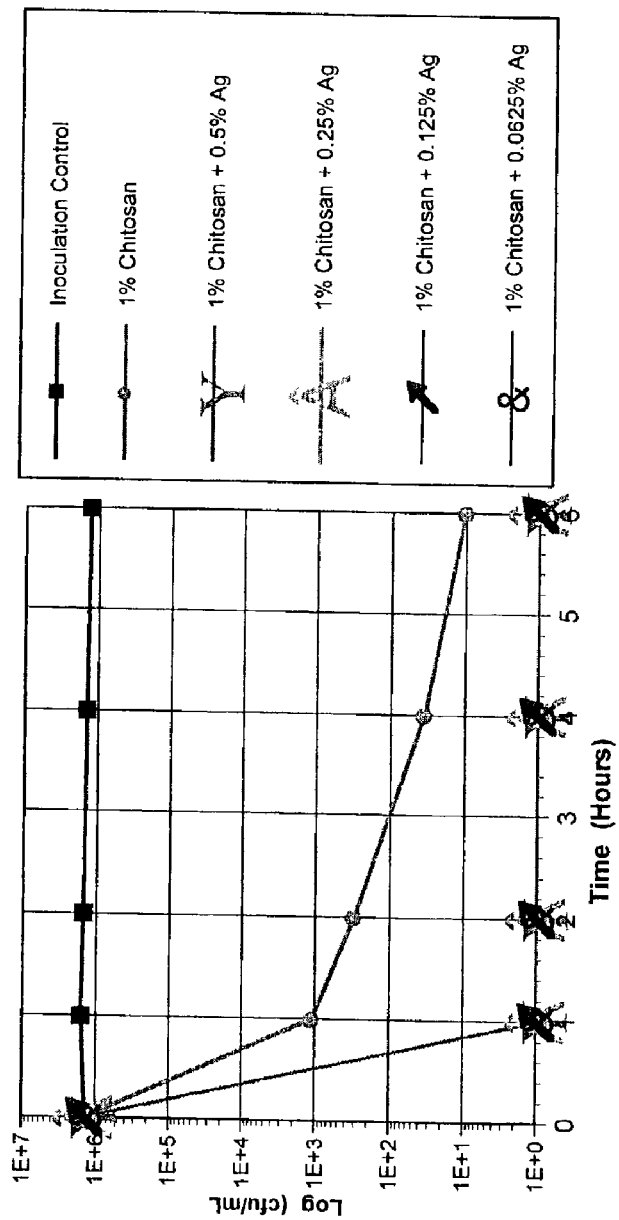
FIG. 9 is a diagram showing the antimicrobial effect of chitosan grafted on 2GT fabrics with various concentration silver nitrate solution post treatment vs. *Staphylococcus aureus* ATCC 6538.
Figure 10:
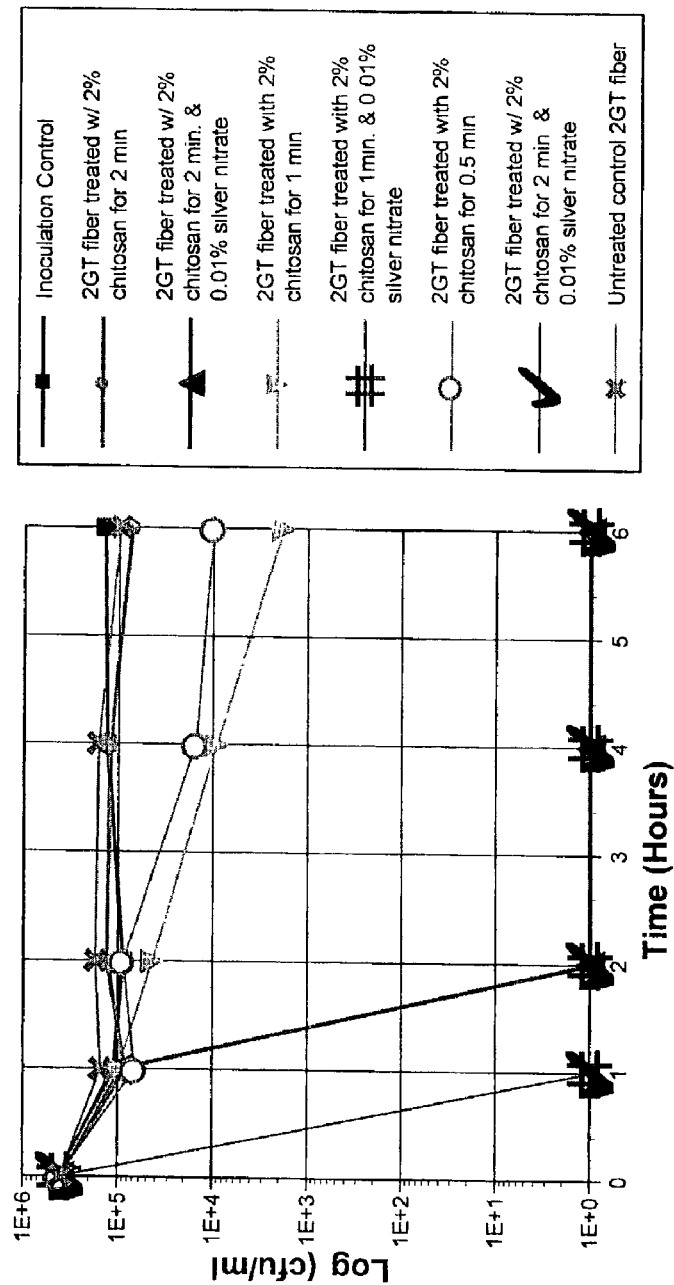
FIG. 10 is a diagram showing the antimicrobial effect of chitosan grafted on 2GT fabrics after various hydrolysis times with and without a 0.1% silver nitrate post treatment vs. *E. coli* O157:H7.

Four samples were, respectively, treated with aqueous 0.5%, 0.25%, 0.125%, and 0.0625% silver nitrate solution for 2 min., washed with water and dried at 45 C. for 16 h. The antimicrobial activity of these 4 samples and the "chitosan-only" control were then evaluated. FIG. 9 shows the antimicrobial effect of these 5 samples vs. *Staphylococcus aureus* ATCC 6538. Even the lowest concentration of silver nitrate (0.0625%) is very efficacious against the microbe *Staphylococcus aureus* ATCC 6538 and, as shown in FIG. 10, just 0.01% silver nitrate dope was efficacious against microbes that can only be killed with chitosan-silver, such as *E. coli* O157:H7. It is postulated that the low concentration of silver works in synergy with the chitosan to achieve this level of efficacy.

Example 5

Preparation of Chitosan Grafted Fabrics Employing Various Times of Chitosan Treatment With and Without 0.1% Silver Nitrate Post Treatment Samples of 2GT fibers were hydrolyzed and treated with 2% chitosan by the procedure of Example 4 except that the chitosan treatment time was 0.5, 1 or 2 minutes, respectively. Portions of each of these three samples were then treated with a 0.1% silver nitrate solution as in Example 4. FIG. 10 shows the antimicrobial effect of chitosan grafted on 2GT fabrics after these various hydrolysis times with and without the 0.1% silver nitrate post treatment vs. *E. coli* O157:H7.

Example 6

Wash Testing of Chitosan Grafted 3GT Fabrics (With and Without Silver Nitrate Post-Treatment)

Samples of 3GT chitosan grafted fabrics, with and without silver nitrate treatment (3GT samples prepared in Example 3 and Example 1, respectively), were subjected to five AATCC RA 88 "C" wash cycles. Table 1 below shows the results of an *E. coli* ATCC 25922 shake flask test on these washed 3GT fabrics. The Δt is the log reduction between the inoculum control and the test material. As shown in Table 1, all chitosan and chitosan+silver-treated fabrics reduced the viable population of *E. coli* ATCC 25922 by at least 3 logs after 4 h of exposure.

TABLE 1

3GT woven fabrics prepared with grafted chitosan with and without a silver nitrate post treatment vs. *E. coli* ATCC 25922.

| Fabric | Δt after 1 h | Δt after 4 h |
| --- | --- | --- |
| 3GT Control, unwashed | 0.000 | 0.000 |
| 3GT Control, washed | 0.267 | 0.160 |
| 3GT + Chitosan, unwashed | 4.869 | 5.415 |
| 3GT + Chitosan, washed | 2.313 | 3.813 |
| 3GT + Chitosan + Ag, unwashed | 5.568 | 5.415 |
| 3GT + Chitosan + Ag, washed | 5.568 | 5.415 |

Example 7

Testing of Antimicrobial Activity of Free Chitosan, Chitosan Grafted 2GT and Silver Nitrate Post-Treated Chitosan Grafted 2GT Two pieces of scoured socks (5.56 g and 5.9 g respectively) of 2GT polyester fabrics were grafted with 2% chitosan solution as described in Example 1 to generate chitosan grafted fabrics (weight after grafting was 6.2 g and 6.6 g, respectively). This latter piece of fabric (6.6 g) was then soaked with 0.5% silver nitrate solution, washed with water and dried at 37° C. for 16 h. Weight of the dried fabric was 6.6 g. For comparative purposes, free chitosan powder was tested as is in the shake flask test.

Figure 11:
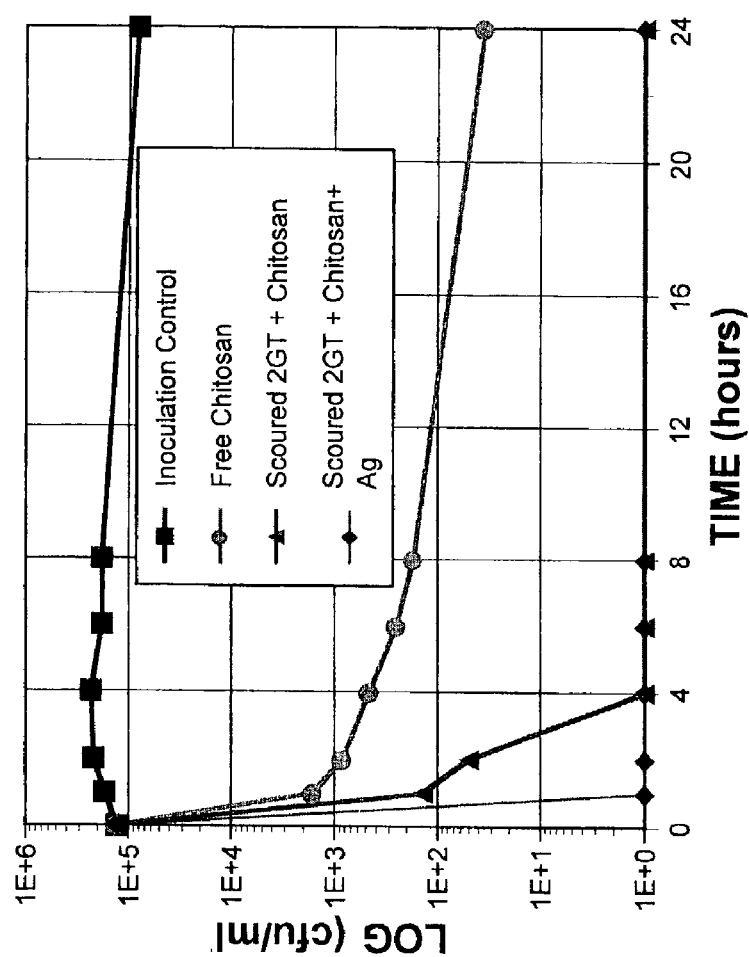
FIG. 11 is a diagram showing the antimicrobial activity of free chitosan vs. grafted chitosan on 2GT fabric vs. *Staphylococcus aureus* ATCC 6538.

FIG. 11 shows the antimicrobial activity of free chitosan, grafted chitosan and silver nitrate-treated grafted chitosan vs. *Staphylococcus aureus* ATCC 6538. Free chitosan demonstrates lower antimicrobial activity, which is more characteristic of a bacteriostat, compared to chitosan grafted onto polyester with or without silver nitrate post treatment.

Example 8

Multi-layer Grafting of 2GT Fabrics With Chitosan and Polyacrylic Acid

Four 2GT knit fabrics (samples A–D, 19.5, 18.8,19.5, 19.7 g, respectively) were grafted with chitosan as described in Example 1. Weight of the products A–D were 21.3, 20.4, 21.2, and 21.1 g, respectively.

Fabric samples A and B were dipped in 2% polyacrylic acid solution for 30 min, air dried and washed with water and then dried at 80° C. to give chitosan polyacrylic acid coated fabrics A' (21.5 g) and B' (20.6 g).

Part of fabric A' (10.3 g) was treated again with 2% chitosan solution and dried at 85° C. for 16 h followed by washing with water and dried to give A" (10.5 g). Another part of A' (11.2 g) was dipped in 2% silver nitrate solution for 30 min, washed with water and dried at 37° C. for 16 h. to give A'''. Weight of A''' was 11.02 g.

Figure 12:
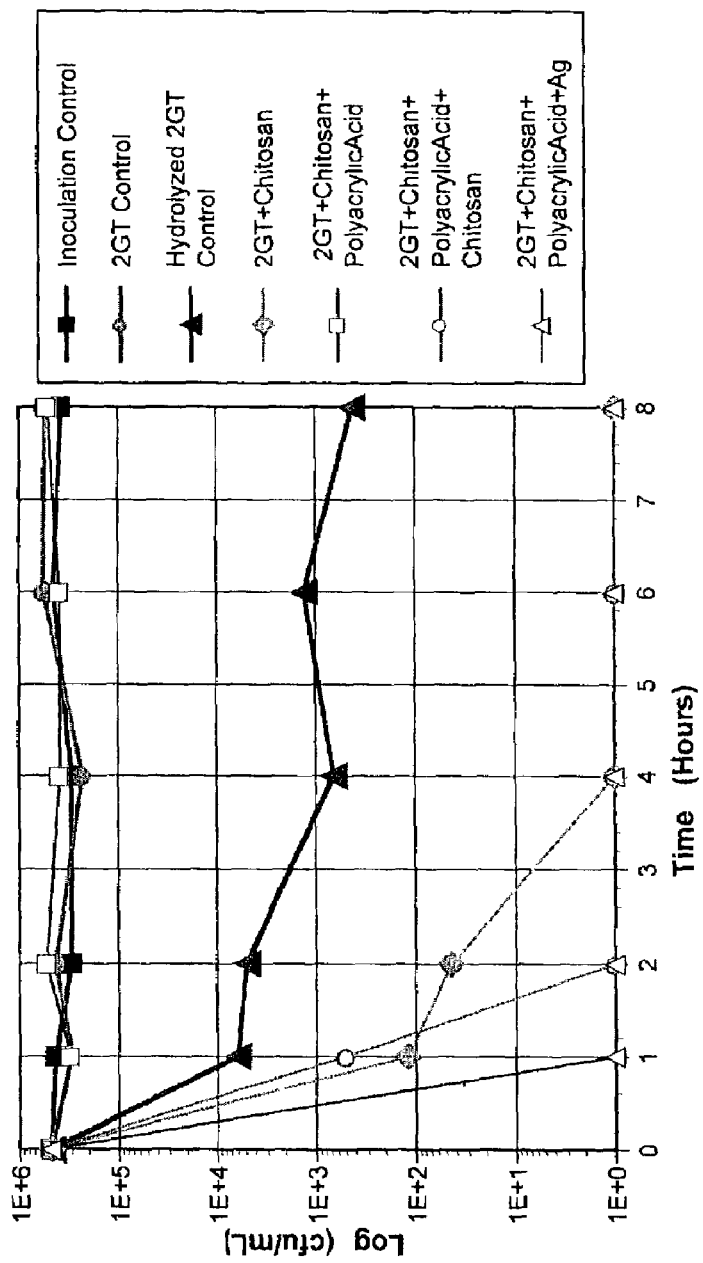
FIG. 12 is a diagram showing the antimicrobial activity of grafted chitosan on 2GT knit fabrics with various after-treatments of polyacrylic acid, additional chitosan and/or silver nitrate treatment vs. *E. coli* 25922.

FIG. 12 shows the antimicrobial activity of 2GT+chitosan (A); 2GT+chitosan+polyacrylic acid (A"); 2GT+chitosan+ polyacrylic acid+chitosan (A"), and 2GT+chitosan+polyacrylic acid;+silver nitrate (A''') and three various controls vs. *E. coli* 25922.

Example 9

Chitosan Grafted Fibers Made in Commercial Prototype Equipment

The chitosan chemistry described in the above examples can be applied to fibers as well as fabrics using standard fiber processing equipment. The preparation of antimicrobial fibers by performing the caustic hydrolysis, acidification, and chitosan grafting steps in a package dyer, as well as by performing the caustic hydrolysis and acidification in a package dyer and the chitosan grafting step in a single-end sizer machine has been demonstrated.

Figure 13:
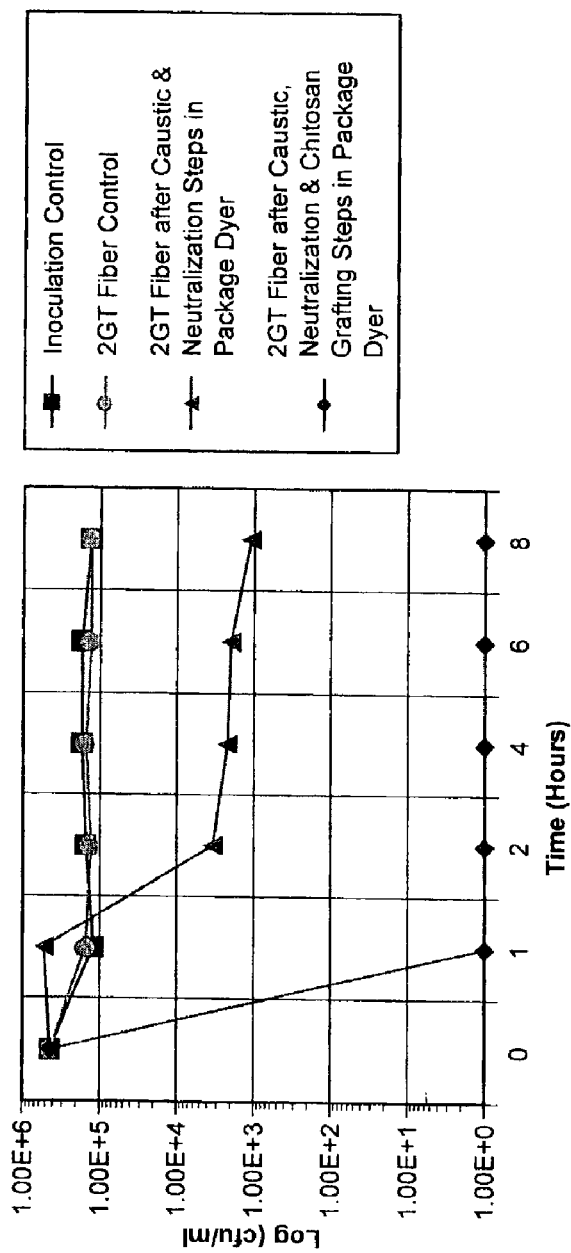
FIG. 13 is a diagram showing the antimicrobial effect of chitosan grafted on 2GT fiber by processing in a package dyer vs. *E. coli* ATCC 25922.
Figure 14:
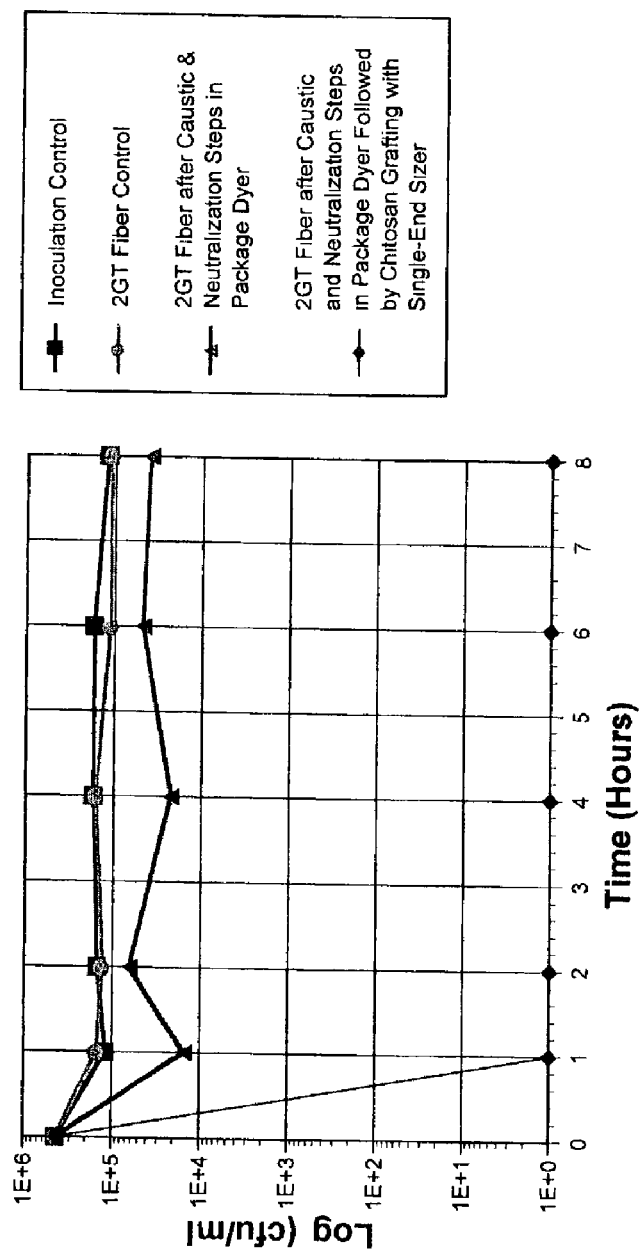
FIG. 14 is a diagram showing the antimicrobial effect of chitosan grafted on 2GT fiber by processing in a package dyer and single-end sizer vs. *E. coli* ATCC 25922.

FIG. 13 shows antimicrobial performance of 2GT fiber with grafted chitosan applied by processing in a package dyer vs. *E. coli* ATCC 25922. FIG. 14 shows the antimicrobial performance of 2GT fiber with grafted chitosan applied by processing in a package dyer and single-end sizer vs. *E. coli* ATCC 25922.

Example 10

Chitosan-Treated Bicomponent Fiber: 2GT/Lycra® Blend

Figure 15:
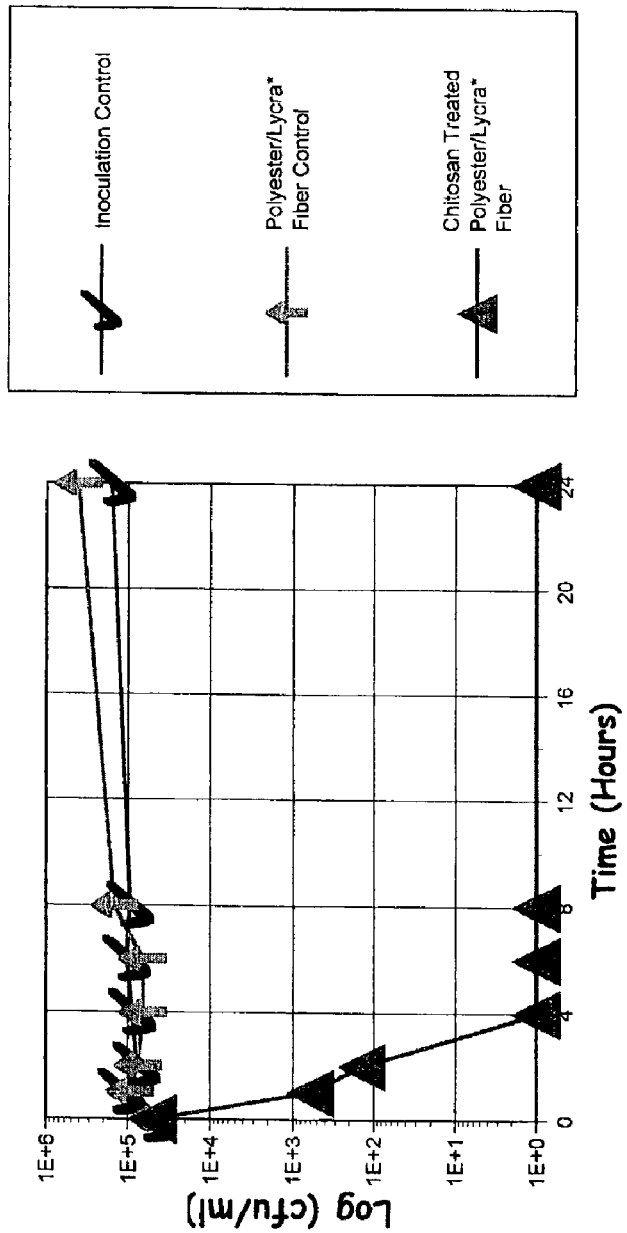
FIG. 15 is a diagram showing the antimicrobial effect of a chitosan-treated polyester and Lycra® blend fiber vs. *E. coli* ATCC 25922.

Fibers of a Lycra® spandex/2GT blend (Lycra® spandex/ 2GT blend fiber containing 10% 10 denier Lycra® and 90% 150 denier Dacron® polyester, made by E. I. du Pont de Nemours and Company (Wilmington, Del.)) were treated with caustic as described in Example 1. The treated fibers were then passed through a chitosan solution in a single-end sizer as in Example 9. FIG. 15 shows the antimicrobial effect of the chitosan-treated fibers versus *E. coli* ATCC 25922.

Example 11

Chitosan Treatment of Yarns Commonly Combined with Polyester in Fabrics

Figure 16:
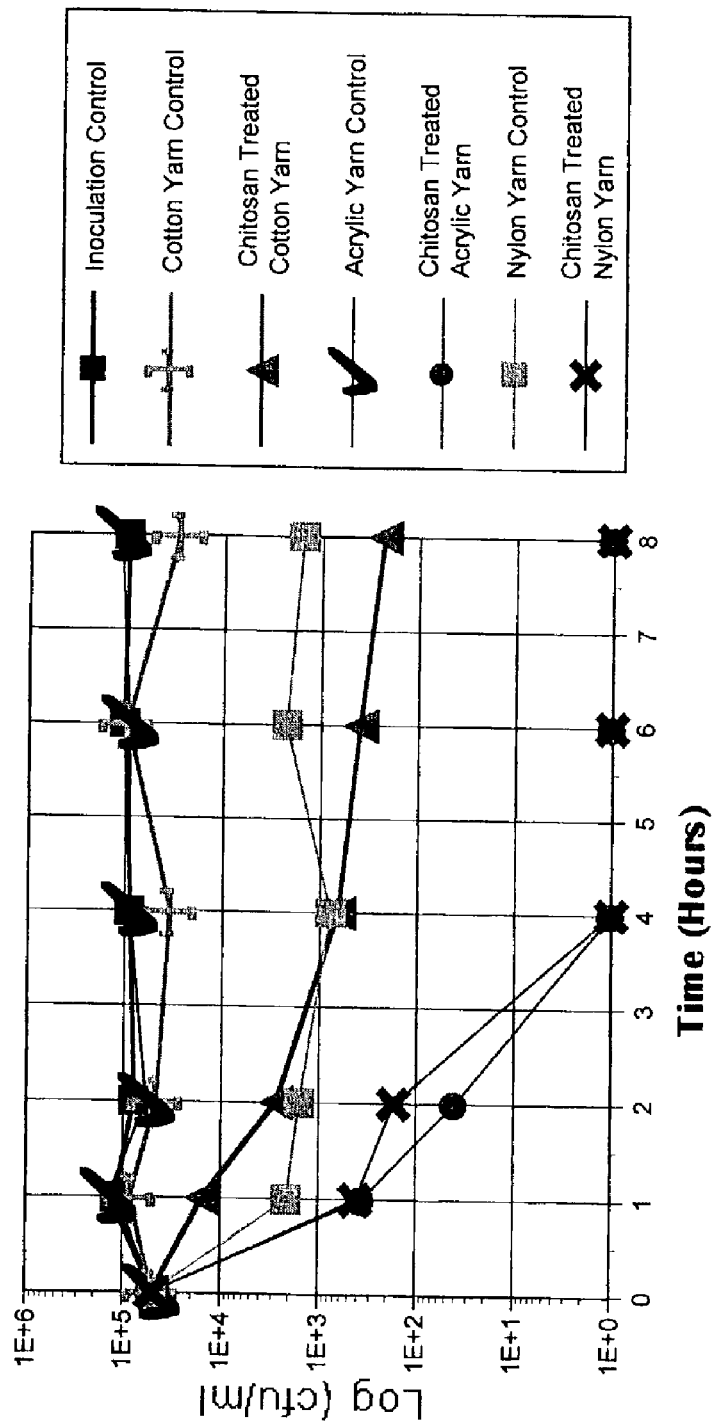
FIG. 16 is a diagram showing the antimicrobial effect vs. *E. coli* ATCC 25922 of chitosan treatment of yarns commonly occurring in polyester blends.

Cotton yarn (having a yarn count of 30/1cc, commercially available from Parkdale Mills, Inc. (Gastonia, N.C.)), Soft White® 24 acrylic yarn (1/24 worsted count with a 1½" cut, 100% open end spun yarn that has been waxed, made by Amital Spinning Corporation (New Bern, N.C.)), and Tactel® nylon 66 (30 denier yarn (commercially available from E. I. du Pont de Nemours and Company, Wilmington, Del.) were treated with caustic as described in Example 1. The treated fibers were then passed through a chitosan solution in a single end sizer as in Example 9. FIG. 16 shows the antimicrobial effect of the chitosan-treated yarns versus *E. coli* ATCC 25922.

Example 12

Chitosan-Treated Polyester/Rayon Nonwoven Fabric

Figure 17:
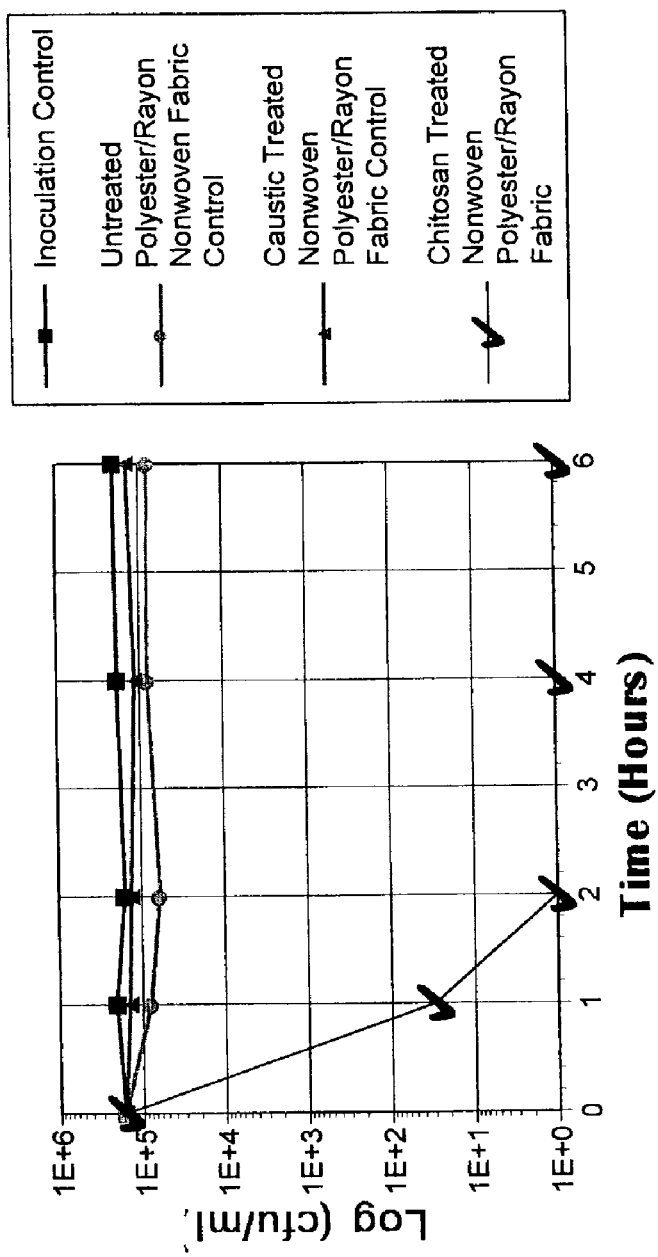
FIG. 17 is a diagram showing the antimicrobial effect of a chitosan-treated polyester/rayon nonwoven fabric vs. *E. coli* ATCC 25922.

Sontara® wipes comprising a 1:1 polyester/rayon nonwoven blend (commercially available from E. I. du Pont de Nemours and Company. (Wilmington, Del.) were treated as in Example 1, one sample with only the caustic treatment described therein and one with the complete chitosan grafting treatment. The antimicrobial effect of the chitosan grafting treatment versus *E coli* ATCC 25922 is seen in FIG. 17.

Example 13

Chitosan-Treated Polyester/Cellulose Nonwoven Fabric

Figure 18:
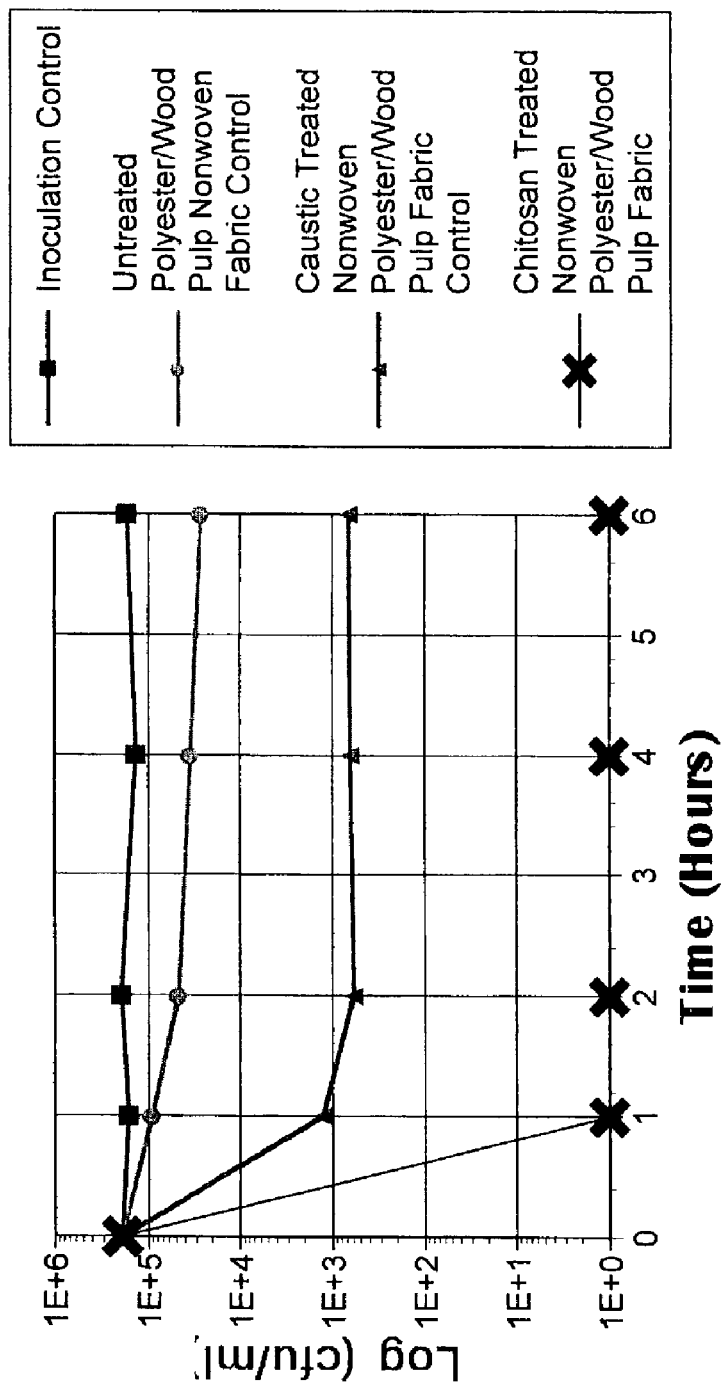
FIG. 18 is a diagram showing the antimicrobial effect of a chitosan-treated polyester/wood pulp nonwoven fabric vs. *E. coli* ATCC 25922.

Sontara® wipes comprising a 1:1 polyester/wood pulp nonwoven blend (commercially available from E. I. du Pont de Nemours and Company, Wilmington, Del.) were treated as in Example 1, one sample with only the caustic treatment described therein and one with the complete chitosan grafting treatment. The antimicrobial effect of the chitosan grafting treatment versus *E. coli* ATCC 25922 is seen in FIG. 18.

Example 14–18

(a) Preparation of Surface Primed 2GT Fibers

2GT fiber (150–200 g, 229 g) was passed at a rate of about 8 m/min through a series of solution trays containing, in turn, 10% aqueous sodium hydroxide, 1.0 M aqueous hydrochloric acid, and water. Excess solution was then stripped from the fiber with a sponge. The fiber was then dried by wrapping around a drum heated to about 130° C. The fiber was then wound using a tension winder followed by heat setting the fiber at 160° C. by wrapping around a heated roller at that temperature and winding at a speed at 60 m/min. Yield of the fiber was 218.7 g, a loss of 4.5 weight percent. This procedure demonstrates the hydrolysis conditions that cause weight loss of the fiber. The process resulted in the formation of carboxyl groups on the surface of the fiber as evidenced from the dying of the fiber with a blue dye specific for acidic groups.

(b) Preparation of 2GT Chitosan-Treated Fiber and Fabric

2GT fiber (150–200 g) was passed at a rate of about 8 m/min through a series of solution trays containing, in turn, 10% aqueous sodium hydroxide, 1.0 M aqueous hydrochloric acid, water, and a solution of chitosan (Chitoclear®, Primex Ingredients, Norway) in 1% aqueous acetic acid. The concentration of chitosan varied from 0.25 to 2 weight percent, as shown in Table 1. Excess solution was then stripped from the fiber with a sponge. The fiber was dried by wrapping around a drum heated to about 130° C. The fiber was then wound using a tension winder followed by heat setting of the fiber at 160° C. by wrapping around a heated roller at that temperature and winding at a speed of 60 m/min. In each case, the chitosan-treated fiber was tested with Orange II dye, and the orange color indicated chitosan was present on the surface of the fiber. A portion of fiber that had been treated with a 2% chitosan solution was made into a fabric and dyed with Orange II dye. The intense orange color indicated that chitosan was present at the surface of the fabric.

TABLE 2

| Example | Initial Weight (g) | Final Weight (g) | Weight Change (%) | Chitosan Concentration (weight %) |
|---|---|---|---|---|
| Surface primed only | 229 | 218.7 | −4.5 | 0 |
|  |  |  | −4.5 |  |
| 14 | 207 | 231 | 11.6 | 2 |
| 15 | 141 | 154 | 9.2 | 1.5 |
| 16 | 165 | 174 | 5.5 | 1 |
| 17 | 119 | 133 | 11.8 | 0.5 |
| 18 | 216 | 237 | 9.7 | 0.25 |

Example 20

Preparation of Antimicrobial Chitosan-2GT/3GT Fibers

Figure 19:
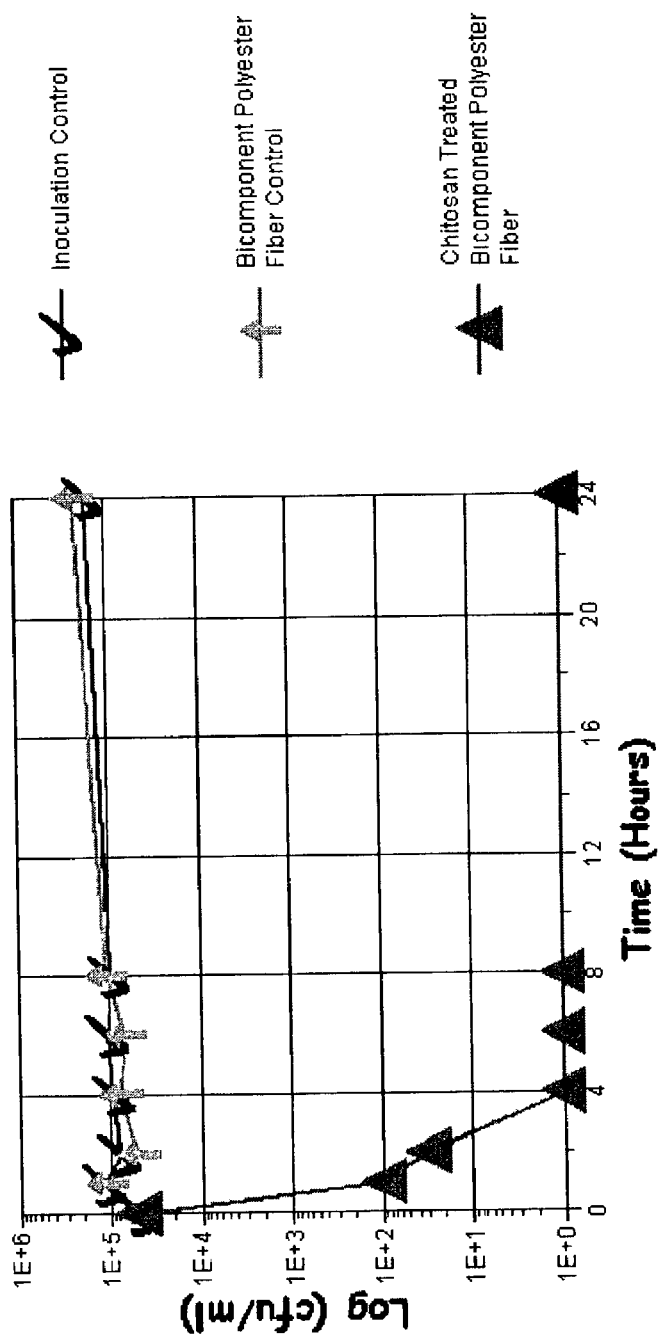
FIG. 19 is a diagram showing the antimicrobial effect of a chitosan-treated bicomponent (2GT/3GT) polyester fiber vs. *E. coli* ATCC 25922.

2GT/3GT bicomponent fiber from E. I. du Pont de Nemours and Company (Wilmington, Del.) was passed at a rate of about 8 m/min through a series of solution trays containing, in turn, 10% aqueous sodium hydroxide, 1.0 M aqueous hydrochloric acid, water, and a solution of 0.25% chitosan (Chitoclear®, Primex Ingredients ASA, Norway) in 1% aqueous acetic acid. This was followed by stripping the excess solution in the fiber with a sponge. The fiber was dried by wrapping around a drum heated to about 130° C. The fiber was then wound using a tension winder followed by heat setting of the fiber at 160° C. by wrapping around a heated roller at that temperature and winding at a speed at 60 m/min. Two samples were taken from different part of the fiber and submitted for antimicrobial evaluation. The antimicrobial effect of the chitosan grafting treatment versus *E coli* ATCC 25922 is seen in FIG. 19.

What is claimed is:

1. A method for preparing an antimicrobial polyester-containing article having chitosan grafted thereon comprising the sequential steps of:
   (a) providing a polyester-containing article;
   (b) contacting the polyester-containing article with a basic solution;
   (c) optionally, washing the article produced in step (b);
   (d) contacting the article produced in step (b) or step (c) with a strong mineral acid solution;
   (e) optionally, washing the article produced in step (d);
   (f) contacting the article produced in step (d) or step (e) with a solution comprising a chitosan agent selected from the group consisting of chitosan, chitosan salts and chitosan derivatives wherein the chitosan is grafted thereon the polyester-containing article;
   (g) optionally, heating the article produced in step (f);
   (h) isolating the article produced instep (f) or step (g); and
   (i) optionally, heating the article isolated in step (h) at a temperature higher than the temperature employed in step (g).

2. A method for producing an antimicrobial polyester-containing article having chitosan grafted thereon comprising the sequential steps of:
   (a) providing a feed station on which is disposed a polyester-containing article and a take-up station capable of receiving the polyester-containing article;
   (b) drawing the article from the feed station through a first treatment station wherein said article is exposed to a basic solution;
   (c) optionally, drawing the step (b)-treated article through a second treatment station wherein the article is exposed to water;
   (d) drawing the step (b)- or step (c)-treated article through a third treatment station wherein the article is exposed to a strong mineral acid solution;
   (e) optionally, drawing the step (d)-treated article through a fourth treatment station wherein the article is exposed to deionized water;
   (f) drawing the step (d)- or step (e)-treated article through a fifth treatment station wherein the article is exposed to a solution comprising a chitosan agent selected from the group consisting of chitosan, chitosan salts and chitosan derivatives wherein the chitosan is grafted thereon the polyester-containing article;
   (g) optionally, heating the step (f)-treated article after it exits the fifth treatment station; and
   (h) causing the step (f)- or step (g)-treated article to be received on and accumulate on the take-up station.

3. The method of claim 2 wherein steps (b) and (c) together are performed for a time sufficient to reduce the weight of the article by from 1 to 30 percent.

4. The method of claim 2 wherein steps (b) and (c) together are performed for a time sufficient to reduce the weight of the article by from 1 to 10 percent.

5. The method of claim 1 or claim 2 wherein the basic solution comprises a base selected from the group consisting of soluble Group I hydroxides, soluble Group II hydroxides, soluble Group III hydroxides, ammonium hydroxide, and alkyl-substituted ammonium hydroxides; and the base is dissolved in water or a mixture of water with one or more waler-soluble organic solvents selected from the group consisting of methanol, ethanol, propanol, ethylene glycol, propylene glycol, acetonitrile, dimethylformamide, and dimethylacetamide.

6. The method of claim 1 or claim 2 wherein step (b) is performed at a temperature of from 10° C. to 90° C.

7. The method of claim 1 or claim 2 wherein the strong mineral acid solution comprises a strong mineral acid having a pKa less than 2.

8. The method of claim 1 or claim 2 wherein the solution comprising a chitosan agent is a solution of chitosan in a dilute, water-soluble, organic acid selected from the group consisting of mono-, di- and polycarboxylic acids.

9. The method of claim 1 or claim 2 wherein the solution comprising a chitosan agent is chitosan in dilute aqueous acetic acid.

10. The method of claim 9 wherein said solution comprises 0.25% to 5.0% by volume of the dilute aqueous acetic acid and 0.25% to 8.0% of chitosan by weight of the solution.

11. The method of claim 1 wherein the washing of step (c) and of step (e) is performed with deionized water.

12. The method of claim 1 or claim 2 wherein the heating of step (g) is performed at a temperature of from 35° C. to 190° C.

13. The method of claim 1 or claim 2 wherein the heating of step (g) is performed for from 30 seconds to 20 hours.

14. The method of claim 3 wherein the time sufficient to reduce the weight of the article is from 2 seconds to 30 seconds.

15. The method of claim 1 further comprising contacting the article produced in step (f), (g), (h) or (i) with a solution comprising a metal salt; a solution comprising a carboxyl-containing polymer; an additional solution comprising a chitosan agent; or combinations thereof, wherein the surface of the article produced comprises chitosan, a metal salt, or combinations thereof.

16. The method of claim 2 further comprising drawing the step (f)-, (g)-, or (b)-treated article through a subsequent station containing a solution comprising a metal salt; a solution comprising a carboxyl-containing polymer; an additional solution comprising a chitosan agent; or combinations thereof, wherein the surface of the article produced comprises chitosan, a metal salt or combinations thereof.

17. The method of claim 15 or claim 16 wherein the metal salt is selected from the group consisting of soluble silver salts, soluble copper salts, and soluble zinc salts.

18. The method of claim 15 or claim 16 wherein the metal salt is selected from the group consisting of silver nitrate, copper sulfate, and zinc sulfate.

19. The method of claim 15 or claim 16 wherein the carboxyl-containing polymer is polyacrylic acid or sodium carboxymethylcellulose.

20. The method of claim 1 or claim 2 wherein the polyester-containing article is in the form of a filament, fiber, yarn, fabric or film.

21. The method of claim 1 or claim 2 wherein the polyester is selected from the group consisting of poly(ethylene terephthalate), poly(trimethylene terephthalate), poly(tetramethylene terephthalate, and copolymers and blends thereof.

22. The method of claim 1 or claim 2 wherein the polyester-containing article is in the form of a bicomponent fiber consisting essentially of poly(ethylene terephthalate) and poly(trimethylene terephthalate).

23. An antimicrobial polyester-containing article produced by the method of claim 1.

24. An antimicrobial polyester-containing article produced by the method of claim 2.

25. The antimicrobial polyester-containing article of claim 23 or 24 further comprising one or more compounds selected from the group consisting of metal salts, carboxyl-containing polymers, and combinations thereof.

26. The antimicrobial polyester-containing article of claim 25 wherein the surface of the article comprises chitosan, a metal salt or combinations thereof.

27. The polyester-containing article of claim 23 or 24 wherein the polyester is poly(ethylene terephthalate), poly(trimethylene terephthalate), poly(tetramethylene terephthalate), or a copolymer or blend thereof.

28. The polyester-containing article of claim 23 wherein the article is in the form of a bicomponent fiber consisting essentially of poly(ethylene terephthalate) and poly(trimethylene terephthalate).

29. The polyester-containing article of claim 23 or 24 wherein the article is in the form of a filament, fiber, yarn, fabric or film.

30. The polyester-containing article of claim 25 wherein the metal salt is selected from the group consisting of soluble silver salts, soluble copper salts, and soluble zinc salts.

31. The polyester-containing article of claim 25 wherein the metal salt is selected from the group consisting of silver nitrate, copper sulfate, and zinc sulfate.

32. The polyester-containing article of claim 25 wherein the carboxyl-containing polymer is polyacrylic acid or sodium carboxymethylcellulose.

33. An item of apparel comprising the antimicrobial polyester-containing article of claim 24.

34. The item of apparel of claim 33 in the form of sportswear, activewear, intimate apparel, swimwear or medical garment.

35. A healthcare product comprising the antimicrobial polyester-containing article of claim 24.

36. The healthcare product of claim 35 selected from medical drapes, antimicrobial wipes, or personal hygiene product.

37. A counter, floor or wall comprising the antimicrobial polyester-containing article of claim 24.

38. A household article comprising the antimicrobial polyester-containing article of claim 24.

39. A packaging comprising the antimicrobial polyester-containing article of claim 24.

40. An absorbent antimicrobial pad for meat packaging comprising the antimicrobial polyester-containing article of claim 24.

* * * * *